US011730430B2

United States Patent
Alpert et al.

(10) Patent No.: US 11,730,430 B2
(45) Date of Patent: Aug. 22, 2023

(54) SYSTEM AND METHOD FOR SINGLE-SCAN REST-STRESS CARDIAC PET

(71) Applicant: The General Hospital Corporation, Boston, MA (US)

(72) Inventors: Nathaniel Alpert, Plymouth, MA (US); Georges El Fakhri, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 145 days.

(21) Appl. No.: 14/429,178

(22) PCT Filed: Sep. 20, 2013

(86) PCT No.: PCT/US2013/060932
§ 371 (c)(1),
(2) Date: Mar. 18, 2015

(87) PCT Pub. No.: WO2014/047446
PCT Pub. Date: Mar. 27, 2014

(65) Prior Publication Data
US 2015/0230762 A1    Aug. 20, 2015

Related U.S. Application Data

(60) Provisional application No. 61/790,329, filed on Mar. 15, 2013, provisional application No. 61/704,149, filed on Sep. 21, 2012.

(51) Int. Cl.
*A61B 6/03*    (2006.01)
*A61B 6/00*    (2006.01)
(Continued)

(52) U.S. Cl.
CPC .......... *A61B 6/037* (2013.01); *A61B 5/02755* (2013.01); *A61B 5/4884* (2013.01);
(Continued)

(58) Field of Classification Search
CPC ......... A61B 6/037; A61B 5/4884; A61B 6/00; A61B 6/02; A61B 6/04;
(Continued)

(56) References Cited

U.S. PATENT DOCUMENTS 7,848,557 B2 † 12/2010 Kadrmas
2004/0064039 A1* 4/2004 Belardinelli ....... A61K 31/7076
600/431
(Continued)

OTHER PUBLICATIONS

Maddahi et al. "Phase I, First-in-Human Study of BMS747158, a Novel 18F-Labeled Tracer for Myocardial Perfusion PET: Dosimetry, Biodistribution, Safety, and Imaging Characteristics After a Single Injection at Rest" J. Nuclear Medicine vol. 52 No. 9 (2011) pp. 1490-1498.*

(Continued)

*Primary Examiner* — Katherine L Fernandez
*Assistant Examiner* — Farouk A Bruce
(74) *Attorney, Agent, or Firm* — Quarles & Brady LLP

(57) ABSTRACT

The present invention provides a system and method for performing a single-scan rest-stress cardiac measurement. In one aspect, the system includes a positron emission tomography (PET) imaging system, a source of a first PET radiotracer for administration to a subject, a source of a second PET radiotracer for administration to a subject, and a processor. The processor has non-transient computer readable media programmed with instructions to obtain PET images of the subject administered with the radiotracer. Furthermore, the computer readable media is programmed with instructions to process the PET images with a non-steady-state, multi-compartment parametric model. An output of the non-steady-state, multi-compartment parametric model is a measure of myocardial blood flow for both a rest state and a stress state of the subject.

17 Claims, 16 Drawing Sheets

(51) Int. Cl.
*A61B 5/0275* (2006.01)
*A61K 51/04* (2006.01)
*A61B 5/00* (2006.01)

(52) U.S. Cl.
CPC .............. *A61B 6/481* (2013.01); *A61B 6/503* (2013.01); *A61B 6/507* (2013.01); *A61B 6/508* (2013.01); *A61K 51/0459* (2013.01)

(58) Field of Classification Search
CPC ............ A61B 6/481–488; A61B 6/507; A61B 6/5235; A61B 6/5241; A61B 6/42; A61B 5/0275–02755
See application file for complete search history.

(56) References Cited

U.S. PATENT DOCUMENTS

| | | | | |
|---|---|---|---|---|
| 2006/0173301 | A1* | 8/2006 | Darlas | A61B 5/026 600/436 |
| 2008/0230703 | A1* | 9/2008 | Kadrmas | G01T 1/1611 250/363.03 |
| 2012/0089015 | A1* | 4/2012 | Gagnon | G06T 11/006 600/425 |
| 2014/0121511 | A1* | 5/2014 | Kadrmas | A61B 6/482 600/431 |

OTHER PUBLICATIONS

Matthews et al. "Quantitative Dynamic Cardiac 82Rb PET Using-Generalized Factor and Compartment Analyses" Phys. Med. Biol. vol. 42 (2005) pp. 1155-1173.*

El Fakhri et al. "The direct calculation of parametric images from dynamic PET data using maximum-likelihood iterative reconstruction" J. Nucl. Med. vol. 46 (2005) pp. 1264-1271.*

Kisin I.E. ("The effect of Papverine and Dibazol on the Rate of Coronary Circulation", The Laboratory of Regional Pharmacology of the Institute of Pharmacology and Chemotherapy, Academy of Medical Sciences, USSR, Moscow. Sep. 12, 1957, pp. 712-715).*

Yan et al., "Direct 4D List Mode Parametric Reconstruction for PET with a Novel EM Algorithm", IEEE Nucl. Sci. Symp. Conf. Rec. (1997). 2008; 4774103; 3625-3628 (Year: 2008).*

Sherif, et al., "Simplified Quantification of Myocardial Flow Reserve with Flurpiridaz F18: Validation with Microspheres in a Pig Model", The Journal of Nuclear Medicine. vol. 52, No. 4, Apr. 2011, pp. 617-624 (Year: 2011).*

Glover et al., "Comparison Between 201TI and 99mTc Sestamibi Uptake During Adenosine-Induced Vasodilation as a Function of Coronary Stenosis Severity", Circulation. vol. 91, Issue 3, Feb. 1, 1995; pp. 813-820 (Year: 1995).*

International Search Report dated Jan. 30, 2014 in connection with PCT/US2013/060932.

Kamasak M.E. et al., "Direct Reconstruction of Kinetic Parameter Images From Dynamic PET Data", IEEE Transactions on medical imaging, 2005, vol. 24, No. 5, p. 636.

Kadrmas Dan et al., "Single-scan rest-stress cardiac PET imaging with Flurpiridaz F18", J. Nucl. Med., 2012, 53, p. 140.

Wong, Terence Z. et al., "Pet of Hypoxia and Perfusion with 62Cu-ATSM and 62CU-PTSM Using a 62Zn/62Cu Generator," pp. 427-432, Feb. 2008 190(2), American Journal of Roentgenology, American Roentgen Ray Society, Leesburg, VA.†

Yu, Ming et al., "The Next Generation of Cardiac Positron Emission Tomography Imaging Agents: Discovery of Flurpiridaz F-18 for Detection of Coronary Disease," pp. 305-313, Jul. 2011 41(4), Seminars in Nuclear Medicine, Elsevier, Inc., Atlanta, GA.†

* cited by examiner
† cited by third party

Fig. 1A Standard method
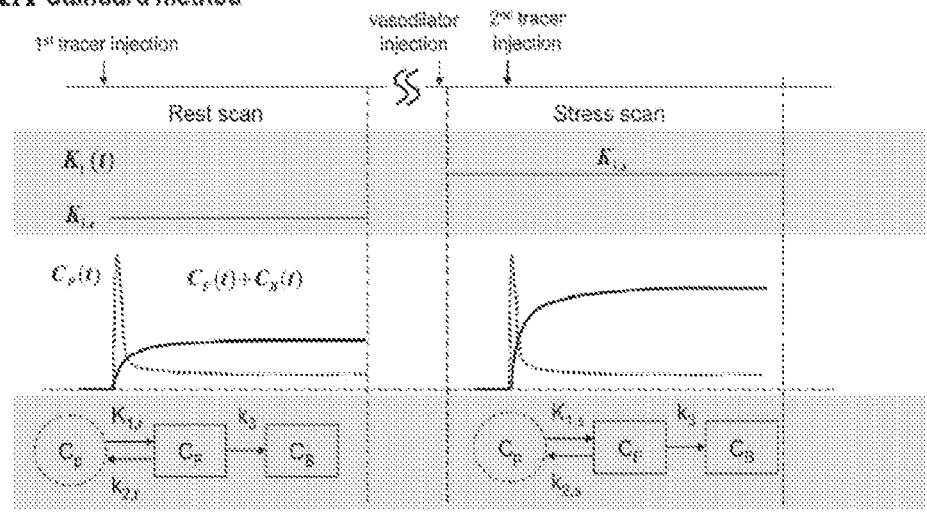
Fig. 1B Rust method
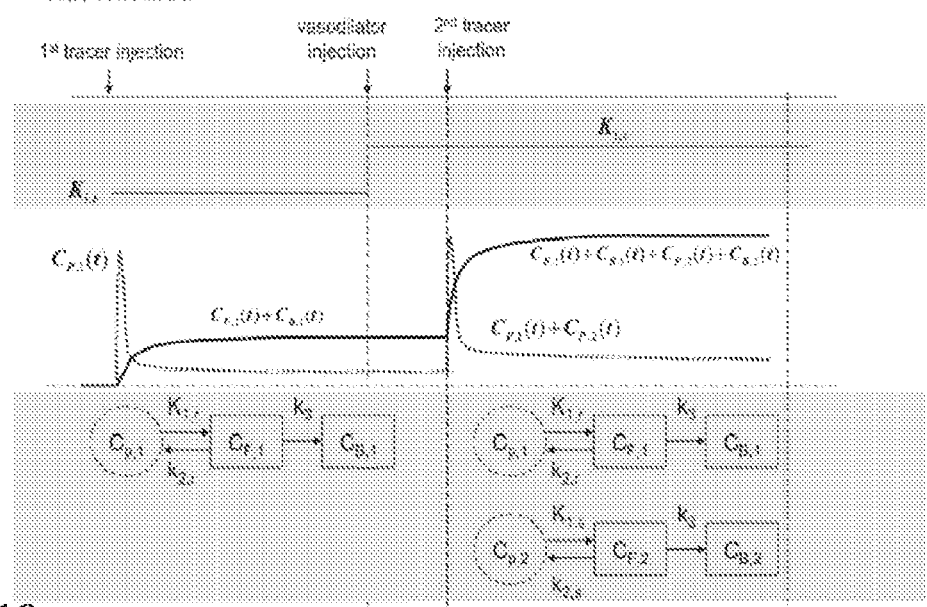
Fig. 1C MGH method
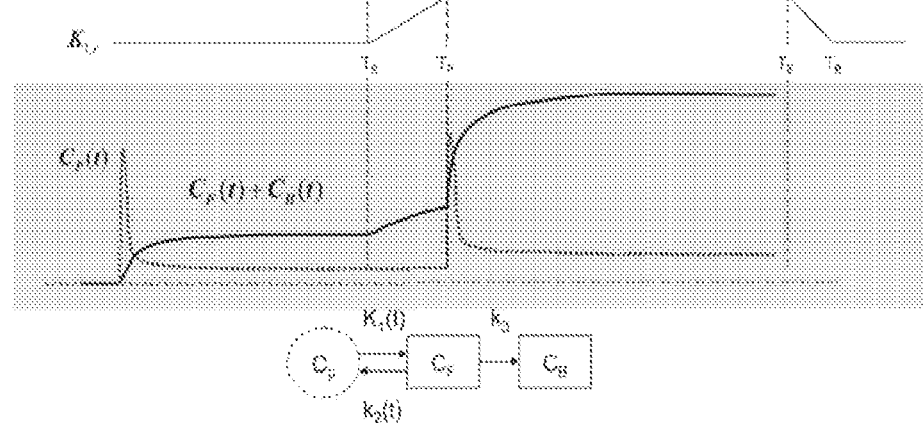

SYSTEM AND METHOD FOR SINGLE-SCAN REST-STRESS CARDIAC PET

CROSS-REFERENCE TO RELATED APPLICATIONS

This application, represents the national stage entry of PCT International Application No. PCT/US2013/060932 filed Sep. 20, 2013, which claims the benefit of U.S. Provisional Patent Application No. 61/704,149, filed Sep. 21, 2012, and U.S. Provisional Application No. 61/790,329, filed Mar. 15, 2013. The disclosures of which are incorporated herein by reference for all purposes.

STATEMENT REGARDING FEDERALLY SPONSORED RESEARCH

This invention was made with government support under NIH R56HL095076 and R01HL110241 awarded by the National Institutes of Health. The government has certain rights in the invention.

BACKGROUND OF THE INVENTION

The disclosure relates, in general, to systems and methods for performing positron emission tomography (PET) and, more particularly, to systems and methods for the development and application of parametric modeling to long half-life tracers, such as $^{18}F$-based tracers for myocardial blood flow (MBF) analysis.

Dynamic measurements with PET are a main stay of research, allowing, for example, absolute measurement of metabolic rates, transport rates, and receptor densities; and yet there are few, if any, clinical applications that make full use of the quantitative capabilities of PET. Clinical applications continue to be based, primarily, on visual inspection of static images.

With respect to clinical significance, coronary artery disease (CAD) represents an enormous public health burden with a prevalence of 7.6% in the US in 2009 and 1.3 million new cases each year. Myocardial perfusion already plays a central role in noninvasive diagnosis, risk assessment, and guiding management decisions of CAD. Specifically, cardiac rest-stress studies have long been used to diagnose and guide treatment of CAD with single photon emission computed tomography (SPECT) and positron emission tomography (PET). Most studies have been qualitative in that the interpretation relies on visual comparison of single images obtained during rest and stress. A long-standing problem is how to temporally separate the spatial distributions of radionuclide laid down during rest and stress. Typically, each rest/stress study includes two tracer injections, one for the baseline condition and one during the stress test. To avoid significant commingling of activity from rest and stress studies, one must delay the start of the stress study for 3-5 half-lives, a delay that adds logistical complexity and cost while inconveniencing the patient. Short-lived positron emitting radiopharmaceuticals offer one solution to this problem but require either an on-site cyclotron for production of $^{15}O$-, $^{13}N$-, $^{11}C$-compounds or, alternatively, an $^{82}Rb$ generator. Therefore, it is desirable to develop the theoretical basis and a practical measurement strategy that allows for fully quantitative measurements of myocardial blood flow (MBF) to be obtained during a single 20-30 min rest-stress imaging session using tracers with long physical half-lives.

This goal is timely because $^{18}F$-based tracers, such as $^{18}F$-Flurpiridaz and $^{18}F$-BFPET, are currently under commercial development for cardiac imaging applications. Previously, the validity of measuring MBF using $^{18}F$-Flurpiridaz with a two-compartment model has been shown by comparison with microsphere reference measurements. Phase III clinical trials of $^{18}F$-Flurpiridaz are now ongoing.

The introduction of new $^{18}F$-labeled tracers provides an opportunity to extend the range of clinical studies to quantitative mapping of function, applications that are better suited to the monitoring of therapy and the staging of disease than are studies based on visual interpretation of static images. The long physical half-life (109 min) of $^{18}F$-based tracers allows for distribution for clinical studies without the necessity for an on-site cyclotron. In addition, contemporary PET cameras have advanced to the point where quantitative measurements of myocardial radioactivity concentration can be made with high temporal sampling and good statistical precision. Because the heart and great vessels can be included in the field of view, it is possible to measure simultaneously the concentration history of activity in the myocardium and ventricular cavities, opening the way for absolute quantitation of local myocardial blood flow during rest and pharmacologically induced stress. However, as explained above, the long half-life of $^{18}F$ also creates a technical challenge for performing both a rest and stress study within a single image session. Furthermore, there are no established and optimized methods suitable for clinical measurement of dynamic function with $^{18}F$-labeled tracers.

Another problem that limits the use of dynamic function measurements in the clinic is the low signal-to-noise ratio (SNR) of parametric images. Low SNR can be accommodated in research studies because the endpoints are averages measured in cohorts of subject; whereas, clinical studies compare the measurement of a single subject against a normative cohort. Thus a higher SNR is required for diagnostic purposes or for monitoring parametric change due to therapy.

Although precise in nature, invasive approaches are limited by the risks associated with coronary artery catheterization. Myocardial perfusion SPECT and PET remain amongst the most widely used non-invasive methods to evaluate microvascular function in patients with obstructive CAD. However, clinical SPECT and nonquantitative PET are limited in detecting blood flow abnormalities when there is uniform global reduction of myocardial blood flow (MBF), as they can only assess relative differences. This scenario occurs in patients with left main or triple vessel coronary artery disease, as well as with diffuse endothelial and/or microvascular dysfunction, and yields "balanced ischemia", i.e., uniform global reduction in tracer uptake during hyperemic stress. They are also limited when monitoring the response to therapy, due to the necessity of visual analysis rather than absolute quantitation of blood flow.

From a strictly technical point of view, the field is positioned to make a transition to more quantitative imaging. Contemporary PET cameras are capable of dynamic measurements. Computational resources are adequate. Among other things, what is lacking is an adequate SNR in parametric images and a compelling application, one that can achieve wide clinical utilization.

SUMMARY OF THE INVENTION

The present invention overcomes the aforementioned drawbacks by providing a system and method for obtaining both rest and stress blood flow measurements during for example, a single scan session that may last approximately 20 to 30 minutes. An $^{18}$F-labeled tracer may be used to perform the PET process.

In a first embodiment, a system is provided for performing a single-scan rest-stress cardiac measurement. The system includes a positron emission tomography (PET) imaging system, a source of a first PET radiotracer for administration to a subject, a source of a second PET radiotracer for administration to a subject, and a processor having non-transient computer readable media programmed with instructions to obtain PET images of the subject administered with the radiotracer. The computer readable media is further programmed with instructions to process the PET images with a non-steady-state, multi-compartment parametric model. An output of the non-steady-state, multi-compartment parametric model is a measure of myocardial blood flow for both a rest state and a stress state of the subject.

In one aspect, the PET images are acquired during a single scan session on the order of about 20 to about 30 minutes.

In another aspect, at least one of the first and second PET radiotracers has a half-life of at least about 60 minutes. In some embodiments, at least one of the first and second PET radiotracers is an $^{18}$F-based tracer. In other embodiments, the $^{18}$F-based tracer is $^{18}$F-Flurpiridaz.

In a second embodiment, a system is provided for performing a single-scan rest-stress cardiac measurement. The system includes a positron emission tomography (PET) imaging system, a source of a first PET radiotracer for administration to a subject, a source of a second PET radiotracer for administration to a subject and a processor having non-transient computer readable media. The media is programmed with instructions to obtain PET listmode data from the subject administered with the radiotracer and instructions to process the PET listmode data by way of a direct parametric reconstruction (DPR) of kinetic parameters from the listmode data. An output of the DPR is a measure of myocardial blood flow for both a rest state and a stress state of the subject.

In a third embodiment, a system is provided for estimating kinetic parameters of blood flow of a subject. The system includes a source of a PET radiotracer for administration to a subject, a positron emission tomography (PET) imager, and a processor having non-transient computer readable media programmed with instructions to obtain PET image data from the subject. The PET image data is acquired and timed with at least one real-time measurement of a physiological variance of the subject. The system further includes a model for estimating kinetic parameters within of a kinetic region of interest in the PET image data. The kinetic parameters are based on an expression of the radiotracer within the PET image data, and the model is stored in the non-transient computer readable media. The product of the model is a report within non-transitory computer readable memory of at least one kinetic parameter of blood flow based on the kinetic parameters estimated from the PET image data.

In one aspect, the kinetic parameters are based on a real-time measurement of physiological variance of the subject. In another aspect, the model is capable of executing a direct parametric reconstruction (DPR) of the kinetic region of interest. In yet another aspect, the at least one kinetic parameter of blood flow comprises myocardial blood flow during both rest and stress states of the subject. In still another aspect, the radiotracer is administered prior to the rest state and again prior to the stress states of the subject. In some embodiments, the stress state is induced pharmacologically.

In a further aspect, the PET image data is acquired within a total time period of about 30 minutes or less. In another aspect, the at least one real-time measurement of a physiological variance of the subject comprises a computation of ventricle input functions. In some embodiments, the computation of ventricle input functions comprises generalized factor analysis and dynamic orthogonal grouping.

In still other aspects, the radiotracer permits multi-compartment kinetic modeling and has a high first-pass extraction rate with few or slow biochemical reactions. In some embodiments, the few or slow biochemical reactions result in long tissue residence periods. In yet other aspects, the multi-compartment kinetic modeling is extended to include time varying parameters reflecting the both rest and stress conditions. In one aspect, the radiotracer comprises $^{18}$F-Flurpiridaz. In another aspect, the DPR comprises incorporation of time-of-flight information pertaining to the PET images.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 1A-1C are graphic representations showing experimental diagrams of the traditional or standard method for PET rest-stress tests (FIG. 1A), a Rust method for PET rest-stress tests (FIG. 1B), and a method in accordance with the present invention (FIG. 1C), including the injection time-line, time-dependence of MBF, blood and tissue time-activity curves and the compartment models.

FIG. 2A shows $K_1$ as a function of study duration. FIG. 2B shows $K_1$ as a function of $k_3$.

FIG. 6A shows the 10-min frame reconstructed image corresponding to 15-25 min of the rest and stress studies as a fused image over the three axes (short axis, vertical and horizontal long axes).

FIG. 6B shows the polar map of the estimated coronary/cardiac flow reserve (CFR) for this subject.

FIG. 12B shows co-registered rest and stress images of the $^{18}$F-Flurpiridaz in clinical cardiac studies. An ischemic defect is present in the inferior-lateral wall of the myocardium.

FIG. 14A shows the myocardial TAC and the model fit. FIG. 14B is a plot of estimated $K_1$ as a function of study duration up to 10 min. Standard deviation is plotted as error bars. FIG. 14C is a plot of estimated $K_1$ as a function of fixed $k_3$.

DETAILED DESCRIPTION OF THE INVENTION

Figure 2A:
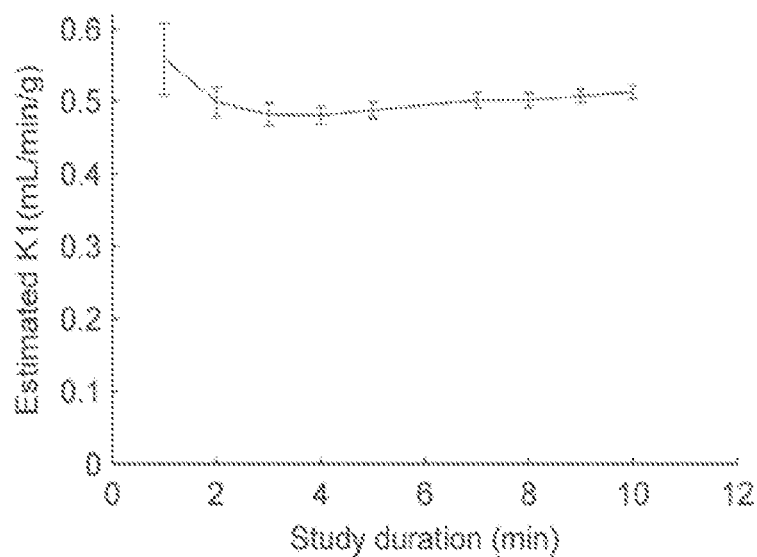
FIGS. 2A-2B are graphs showing the sensitivity analysis of $K_1$ as a function of study duration and $k_3$. The error bars represent the SD estimated from the covariance matrix.

The disclosure relates in general to a system and methods for performing single-scan, rest-stress cardiac PET and, more particularly, to a system and method for the development and application of parametric modeling to long half-life tracers, such as $^{18}$F-based tracers for MBF analysis.

In a first aspect of the present invention, a specific, non-steady state, two compartment model was developed for rest-stress cardiac PET imaging, while a second aspect of the present invention relates to further advanced modeling approaches. With respect to these two aspects of the present invention, the non-steady state modeling approach will be discussed first in order to lay the ground work for the more general discussion the will encompass the advanced modeling approach related to the second aspect of the present invention.

The present system and method is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention.

Any schematic flow chart diagrams included are generally set forth as logical flow-chart diagrams. As such, the depicted order and labeled steps are indicative of one embodiment of the presented method. Other steps and methods may be conceived that are equivalent in function, logic, or effect to one or more steps, or portions thereof, of the illustrated method.

Additionally, the format and symbols employed in any such flow chart diagrams are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Non-Steady State Modeling Approach

In the present application, a system and method are provided for quantifying tracer kinetics, such as 18F-based tracer kinetics, using a PET imaging system. In one embodiment, the system and methods can be applied for quantification of myocardial blood flow (MBF) in a human patient with both rest and stress studies performed in a single scan session having a duration of about 30 minutes. In order to overcome the aforementioned drawbacks, the feasibility of absolute quantification of the MBF within a short, single imaging session was examined by way of kinetic modeling approaches and simulation.

By way of an overview, three procedures for measuring rest/stress myocardial blood flow were analyzed and compared. The procedures are: (1) the Standard method, (2) the Rust method, and (3) the MGH method. In the Standard method, rest and stress measurements are separated in time so that residual radioactivity from the rest studies decays to negligible levels. The Rust method is an adaptation of a previously developed method (Rust, T. C., et al., *Phys. Med. Biol.* 51, 5347-5362, 2006) to analyze MBF measured with $^{13}$N-ammonia, with short decay period between rest and stress. Finally, the MGH method is a protocol that has been newly developed. These procedures feature different experimental protocols, kinetic assumptions, and analytic methods.

The basic methodological approach was to compare the three methods by Monte Carlo simulation. These simulations are based on a digital phantom with anthropomorphic cardio-pulmonary geometry. The simulations produce ensembles of dynamic measurements that realistically predict both the four-dimensional evolution of $^{18}$F-concentrations and the statistical noise propagation for a variety of cardiac abnormalities in different myocardial segments and with different flow responses. The simulations are designed to compare the noise-to-signal ratio of flow measurements for the Standard method versus the MGH method of combined rest-stress. The effect of non-steady-state response to vasodilation was included in the simulations to investigate the effects on estimation bias. The ensembles of simulated studies were analyzed according to the Standard and MGH methods described above, to determine the mean and standard deviation of MBF.

Prior to describing the results of Monte Carlo simulations, the basic optimization of the MGH method with $^{18}$F-Flurpiridaz was considered. The first question addressed is the effect of shortening the observation time: short observation time ensures that the curves depend primarily on flow, but with the trade off of higher noise levels; whereas protocols with longer measurement times may yield better signal-to-noise ratio but must account for the reaction of Flurpiridaz with the mitochondrial complex I. Next, the effect of imperfect knowledge of $k_3$ on the estimation of $K_1$ was studied. Finally, the noise propagation and bias in $k_2$ was studied for the case where the measurement period is short compared to $\ln(2)/k_2$.

The combined rest-stress measurement protocol is described with reference to FIG. 1. Referring first to FIG. 1A, a conceptual diagram of the Standard method is shown in which the rest study and stress study were performed on separate occasions to ensure that no residual activity from the rest study appeared during the stress measurement. The first panel in FIG. 1A shows the time-line of the separated rest and stress studies, with arrows indicating the injection times. At least ten half-lives between the two studies were allowed for tracer decay. The second panel shows that $K_1$ has different constant values in rest ($K_{1,r}$) and stress ($K_{1,s}$). The third panel sketches the expected concentration histories for the input function and the tissue curve along with their relation to important fiducial markers, such as start of infusion and the moment of peak stress. For the purpose of the studies, estimation of MBF from the Standard method was assumed to be unbiased. The Standard protocol was also expected to yield the lowest noise estimates of MBF at any fixed radiation dose. As discussed above, the price is logistical complexity, higher cost per rest-stress exam, difference in bed positions and the inconvenience of two separate scan sessions. The Standard method does not account for non-steady-state flow during the stress measurement. Therefore, it may yield a biased estimate of flow during stress imaging.

The conceptual design for the rest-stress imaging protocol developed for rest-stress imaging by Rust et al. is included in FIG. 1B. The first panel shows the time-line of a single-scan rest-stress protocol, with the arrows indicating time of injection. The second panel shows the assumed time dependence of $K_1$. During rest and stress, Rust et al. assume steady state, with different constant values for rest and stress MBF. The third panel sketches the expected shape of the input functions during rest and stress. The fourth panel sketches the compartment model used to describe the tissue activity. Their approach allows the stress study to begin before the activity from the rest study decays away. As shown in FIG. 1B, they assume that the activity from the first injection evolves throughout the entire experimental period unaffected by the pharmacological perturbation. The sketch also shows that, during the stress measurement period, it is the sum of the residual activity from the first injection and the new activity from the second injection, which is measured by the PET camera. The input function from the first injection, $C_{P,1}$, must be known throughout the entire rest-stress measurement period but only the sum of the two injections is measured during the stress period. Extrapolation and subtraction are used to estimate separate input functions. The PET curve is modeled as the sum of rest and stress, using two separate two-tissue models, as detailed herein.

FIG. 1C shows the conceptual design for the newly developed MGH protocol. The same injection protocol as in the Rust method is used: the rest phase, with the first tracer injection followed about 7 to 10 min later by a vasodilator infusion and then the second tracer injection and stress imaging period. The first panel in FIG. 1C shows that during the rest state $K_1$ is constant, but as vasodilator is infused at time $T_s$ blood flow starts to increase, reaches a maximum at peak stress (time $T_P$), and the peak hyperemia ends at time $T_E$. The flow is expected to return to the baseline at $T_B$. In the MGH protocol list mode acquisition starts with the first injection and continues, without interruption, throughout the stress period. At peak stress, the second tracer injection is made. As the whole study duration can be less than 30 min, the residual activity from the first tracer injection is mixed with the activity from the second tracer injection in the period of the stress scan. As shown in the second panel of FIG. 1C, the residual tracer concentration is affected by the infusion of vasodilator even before the second tracer injection as a result of the pharmacological action of the vasodilator. The effect of the vasodilator continues to affect the residual activity throughout the rest of the study. Due to the vasodilator, the subject is now in a non-steady-state with respect to blood flow; that is blood flow may be changing during the measurement. A basic assumption underlying conventional kinetic modeling, constant blood-to-tissue transport rates and fluxes, is no longer valid. Therefore, compartment modeling was extended to allow flow-related parameters to vary with time in response to the action of vasodilators.

Kinetic models were used to analyze the three protocols as shown in FIGS. 1A-1C. While similar kinetic models were used, there are several notable differences in the detailed assumptions. The fourth panel of FIG. 1A depicts the kinetic model underlying the Standard model, which is designed to analyze rest and stress imaging as independent events. The fluxes and rate constants are considered to be fixed at constant values. The compartment diagram for rest imaging is the same for the Rust and MGH models as these two models differ only in how stress imaging is analyzed. The fourth panel in FIG. 1B shows the compartment diagram for stress imaging in the Rust model. The Rust model predicts the PET curve will be the sum of activity from the rest and stress injections. Rust and colleagues assume that the two tracer injections are independent and superimpose a rest and a stress study, each with constant flow, to predict/ simulate the observed composite PET tissue curve. The Rust model does not explicitly model the effect of pharmacological challenge on the first injection. As a result, the Rust model assumes that residual activity from the rest phase of the study is unaffected by the changes wrought by vasodilator challenge. The state equations for the Rust model can be expressed as $$\frac{dC_{F,1}}{dt} = K_{1,r}C_{P,1} - (k_{2,r} - k_3)C_{F,1} + k_4 C_{B,1} \quad \text{(Eq. 1)}$$

$$\frac{dC_{B,1}}{dt} = k_3 C_{F,1} - k_4 C_{B,1}$$

$$\frac{dC_{F,2}}{dt} = K_{1,s}C_{P,2} - (k_{2,s} + k_3)C_{F,2} + k_4 C_{B,2}$$

$$\frac{dC_{B,2}}{dt} = k_3 C_{F,2} - k_4 C_{B,2}$$

where the subscript "1" and "2" denote the activity concentration from the first and second injection, respectively.

In the case of the MGH method, it was first consider how a hypothetical $^{18}$F-tracer gains access to an elemental tissue volume. It was assumed that the tracer is not metabolized in plasma and is free or in instantaneous equilibrium with plasma proteins and possibly other cellular and subcellular constituents. The molar concentration of the tracer in plasma is denoted as $C_p(t)$, irrespective of the number of tracer injections. The inward flux is $K_1(t) \cdot C_p(t)$, where $K_1(t) = F(t) \cdot E$ is the product of the local myocardial blood flow and the unidirectional extraction fraction, E. For simplicity, E was assumed to be a constant, independent of time. The time-varying clearance rate of tracer from tissue to blood is described by $k_2(t)$. The tissue space is conceptualized as two compartments, one representing free tracer, $C_F(t)$, the other compartment representing reacted tracer molecules, $C_B(t)$. Only the free tracer molecules in blood and tissue can respond to changes in blood flow; increases in flow will affect $K_1(t)$ and $k_2(t)$, resulting in observable changes in the kinetic curves measured by the PET camera. The reacted molecules were considered to be unaffected by flow changes and they cause the long tracer residence time in tissue. For generality, the reaction was left unspecified. But, for example, it can represent a receptor binding reaction or the committed step in a metabolic process. For short measurement times, the amount of tracer returning from the reacted pool can be assumed to be negligible.

Analysis of the MGH protocol uses the two tissue-compartment kinetic model, to allow for tracers with high first pass extraction and long tissue residence time. In the MGH protocol, the two-tissue compartment model is extended to include important characteristics of a rest-stress study, as shown in the bottom panel of FIG. 1C: First, the two injections of tracers are treated as a single entity—the input function $C_p(t)$. The ventricular concentration history is measured during the entire study. During the transition from rest to stress there is a change in physiological state. Residual tracer molecules from the rest study can generally not be distinguished from those injected later. Residual activity from the rest study is observed in combination with the radioactivity injected during pharmacologic stress. Second, stress imaging is reconsidered to account for the changes due to the use of vasodilating drugs. In the past, it has been assumed, either implicitly or explicitly, that blood flow changes abruptly from one constant value in the rest condition to a different constant value in the stress condition. However, previous reports have shown that the myocardial blood flow is altered by slow intravenous infusion of vasodilating drugs in a progressive way over 2 to 7 min, depending on the drug. One way to deal with this phenomenon is to assume that $K_1$ and $k_2$ can be represented by smooth functions of time that can be described by a small number of extra parameters. In the simplest case, $K_1$ and $k_2$ could merely undergo a step change but in a more realistic approximation, $K_1$ and $k_2$ are constant during the rest phase and then have a unimodal shape as a result of stress.

Second, the compartment representation was extended for rest-stress applications. As in conventional compartment modeling, the concept that the concentration in a compartment is spatially homogeneous and temporal changes occur simultaneously throughout the compartment was retained. An innovation in this development is that the flow-related transport rates are allowed to change as a function of time. Further, the probability per unit time for transport ($k_3$) into the reacted compartment was assumed to be unaffected by vasodilating drugs. Accordingly, the basic differential equations can be formulated as $$\frac{dC_F(t)}{dt} = K_1(t)C_P(t) - [k_2(t) + k_3]C_F(t) \quad \text{(Eq. 2)}$$

$$\frac{dC_B(t)}{dt} = k_3 C_F$$

where $K_1(t)$ and $k_2(t)$ are functions of time dependent on the pharmaceutical properties of vasodilators. During the rest phase of the study, $K_1$ and $k_2$ are assumed to be constant. Following the infusion of vasodilator, $K_1(t)$ and $k_2(t)$ are represented by time-varying functions, specified with parameters estimated from the PET data. Equation 2 has a closed-form solution given by $$C_F(t) + C_B(t) = e^{-\int_0^t (k_2(z) + k_3)dz} \cdot \int_0^t \left[ e^{\int_0^u (k_2(z) + k_3)dz} K_1(u)C_P(u) \right] du + \quad \text{(Eq. 3)}$$

$$k_3 \int_0^t \left\{ e^{-\int_0^s (k_2(z) + k_3)dz} \cdot \int_0^s \left[ e^{\int_0^u (k_2(z) + k_3)dz} K_1(u)C_P(u) \right] du \right\} ds$$

Two functional forms were considered, namely, MGH1 and MGH2, for parameters $K_1(t)$ and $k_2(t)$. For the MGH1 model, $K_1$ and $k_2$ are altered as a smooth function of vasodilator kinetics, infusion rate, and duration. Two drugs, adenosine and dipyridamole, have been commonly used in clinical studies. It has been reported that during the intravenous infusion of adenosine and dipyridamole, there is a transitional phase of flow increase until peak hyperemia is reached for both vasodilators but the functional form of the transition is unclear. For simplicity it is approximated as a linear function in this work, as shown in the first panel of FIG. 1C. Similarly, once the blood flow begins to decline from peak hyperemia, the transitional change is assumed to be a linear function of time until the baseline flow is reached. $K_1(t)$ is expressed as $$K_1(t) = K_{1,r} u(T_S - t) + \qquad \text{(Eq. 4)}$$
$$\frac{K_{1,r}(T_P - T_S) + (K_{1,s} - K_{1,r})(t - T_S)}{(T_P - T_S)} \times u(T_P - t)u(t - T_S) +$$
$$K_{1,s} u(t - T_P)u(T_E - t) + \frac{K_{1,r}(T_E - T_B) + (K_{1,s} - K_{1,r})(t - T_B)}{(T_E - T_B)} \times$$
$$u(t - T_E)u(T_B - t) + K_{1,r} u(t - T_B)$$

where u(t) is the unit step function. In Eq. (4), four time points are used to describe the transitions: (1) beginning of infusion ($T_S$), (2) peak hyperemia ($T_P$), (3) end of peak hyperemia ($T_E$), and (4) baseline flow ($T_B$). Note that the peak hyperemia may not end right after the end of vasodilator infusion, especially for dipyridamole. The baseline and peak MBF is defined as $K_{1,r}$ and $K_{1,s}$. The same ramp function is also used to describe the time course of $k_2$ with $k_{2,r}$ and $k_{2,s}$ as $k_2$ at the baseline condition and peak hyperemia, $$k_2(t) = k_{2,r} u(T_S - t) + \qquad \text{(Eq. 5)}$$
$$\frac{k_{2,r}(T_P - T_S) + (k_{2,s} - k_{1,r})(t - T_S)}{(T_P - T_S)} \times u(T_P - t)u(t - T_S) +$$
$$k_{2,s} u(t - T_P)u(T_E - t) + \frac{k_{2,r}(T_E - T_B) + (k_{2,s} - k_{2,r})(t - T_B)}{(T_E - T_B)} \times$$
$$u(t - T_E)u(T_B - t) + k_{2,r} u(t - T_B)$$

Although Eq. (5) is realistic in terms of the physiology, using it to estimate the MBF and CFR (cardiac flow reserve) requires prior knowledge or the estimation of $T_P$, $T_E$, and $T_B$ ($T_S$ is fixed and known). In practice, such timing information can be acquired with external monitoring of the blood pressure or by analyzing the ECG signals. To simplify the model and eliminate the need to measure these three time points, a simplified model MGH2 was also formulated by removing the transition of the parameters and assuming the parameters to change their values by an immediate switch at the time of vasodilator infusion, as the time-dependence of $K_1$ and $k_2$ described by $$K_1(t) = \begin{cases} K_{1,r}, & t < T_S \\ K_{1,s}, & t \geq T_S \end{cases} \qquad \text{(Eq. 6)}$$

$$k_2(t) = \begin{cases} k_{2,r}, & t < T_S \\ k_{2,s}, & t \geq T_S \end{cases}$$

Following development, the kinetic models were applied to the observed measurements. Regardless of the kinetic model chosen or the detailed physiologic assumptions, it is desirable to account for the transiently high blood radioactivity concentrations and finite resolution effects that are included in the PET measurements. Some myocardial radioactivity recorded by the PET camera is not due to radioactivity in myocardial tissue. We model this effect and estimate its magnitude as part of the fitting process, according to Eq. (3):

$$PET(t) \approx f_{lv} \cdot C_{lv}(t) + f_{rv} \cdot C_{rv}(t) + \qquad \text{(Eq. 7)}$$
$$e^{-\int_0^t (k_2(z) + k_3) dz} \cdot \int_0^t \left[ e^{\int_0^u (k_2(z) + k_3) dz} K_1(u) C_P(u) \right] du +$$
$$k_3 \int_0^t e^{-\int_0^\mu (k_2(z) + k_3) dz} \times \int_0^\mu K_1(u) C_P(u) e^{\int_0^u (k_2(z) + k_3) dz} du \cdot d\mu$$

where $f_{lv}$ and $f_{rv}$ represent the spillover fractions for left and right ventricles, respectively.

Figure 2B:
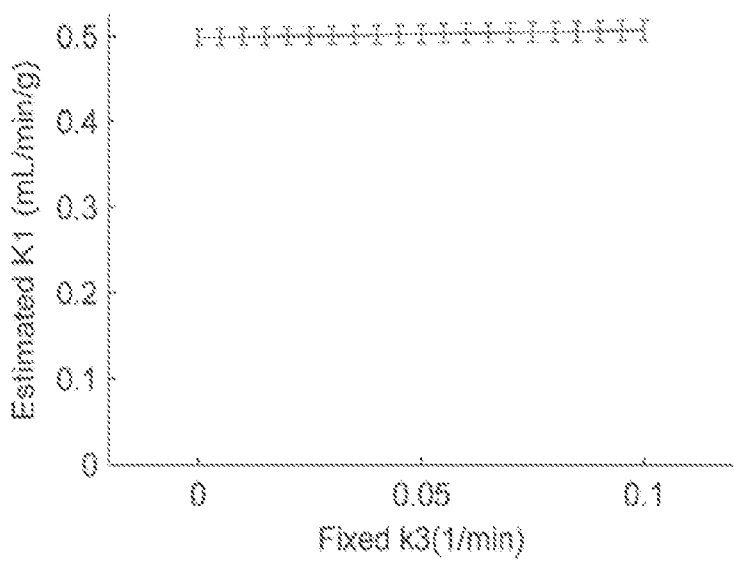

Referring now to the rest of the Figures, the first result deals with estimating blood flow at rest. As expected on theoretical grounds, the part of the PET curve most highly dependent on blood flow was shown to be the initial period after IV injection of $^{18}$F-tracers, such as $^{18}$F-Flurpiridaz. FIG. 2A shows a graph of $K_1$ values versus measurement time for the rest state. The measurement duration varies in 1 min increments, from 1 to 10 min. For short measurements, less than 3 min duration, there is a positive bias. Increasing the measurement period, reduces the statistical error in estimating $K_1$, though gains in signal-to-noise ratio diminish, becoming minimal beyond a 5 min measurement period. The SD of estimated $K_1$ was 2% with 7 min of data and 1.8% with 10 min of data. FIG. 2B shows the variation in estimated $K_1$ as a function of the nominal value of $k_3$. The result clearly shows that $K_1$ is nearly the same (ranged from 0.498 to 0.507), for $k_3$ values between 0 and 0.1 min$^{-1}$.

The clearance rate for tracer from tissue to blood is represented by $k_2$. Simulations demonstrated that a longer measurement period is needed to achieve stable $k_2$ values and lower noise levels in the estimates. With 7 to 10 min of data, the SD for $k_2$ was 10.4% and 6.2%. A strong positive correlation between $k_3$ and $k_2$ was also found where fixing $k_3$ at higher values increases the least squares estimate of $k_2$.

Figure 3:
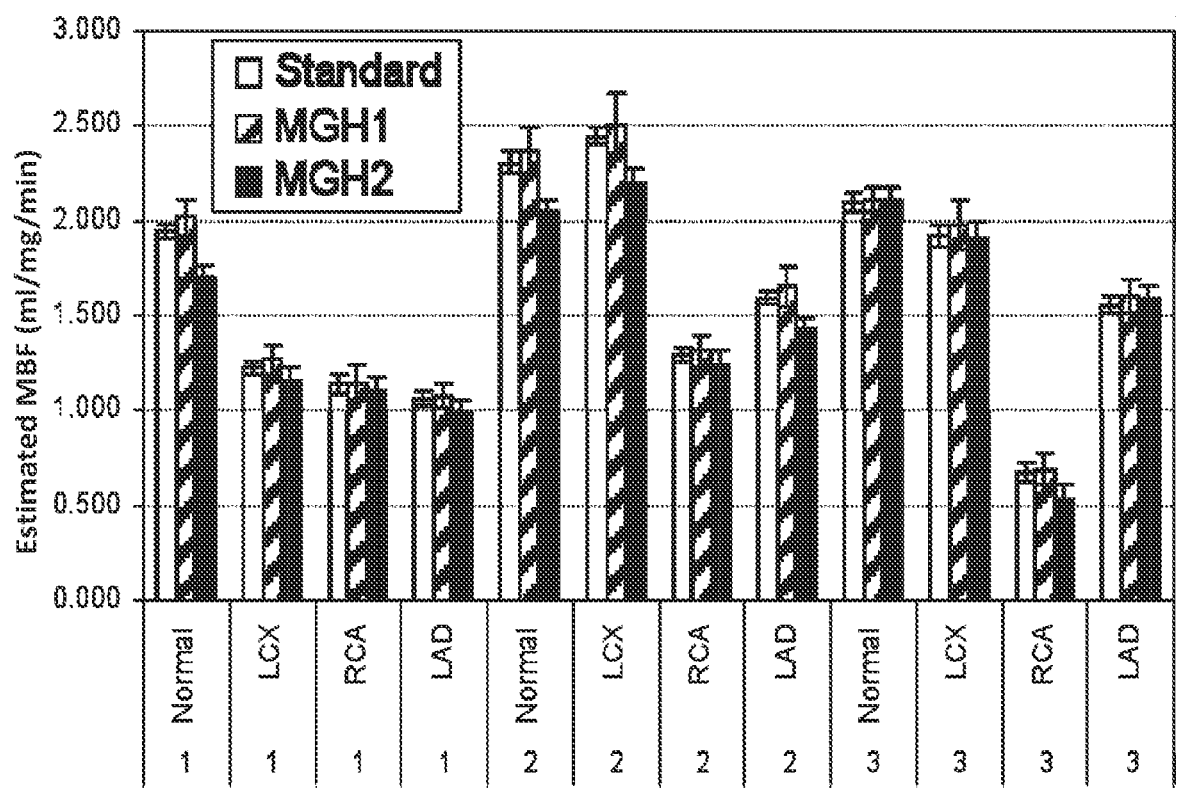
FIG. 3 is a bar graph showing the estimated MBF when dipyridamole is used as the stressor. The second tracer injection dose is equal to the first tracer dose. On the x-axis, the number 1-3 denote the simulation performed based on different representative subjects.

Bar graphs are presented in FIG. 3 summarizing the range of simulated abnormal responses to dipyridamole stress. The injected doses for FIG. 3 for the two tracer injections were identical. The different stress models/protocols include: (1) simulations of stress only as the Standard method, (2) simulations of MGH1, the piecewise linear ramp, and (3) simulations of MGH2, with step-change in flow between rest and stress. Estimates from the MGH1 were found to be close to the estimates from the Standard method in all combinations. MGH2, on the other hand, shows a greater bias in some simulations, usually modest underestimation of MBF.

Figure 4:
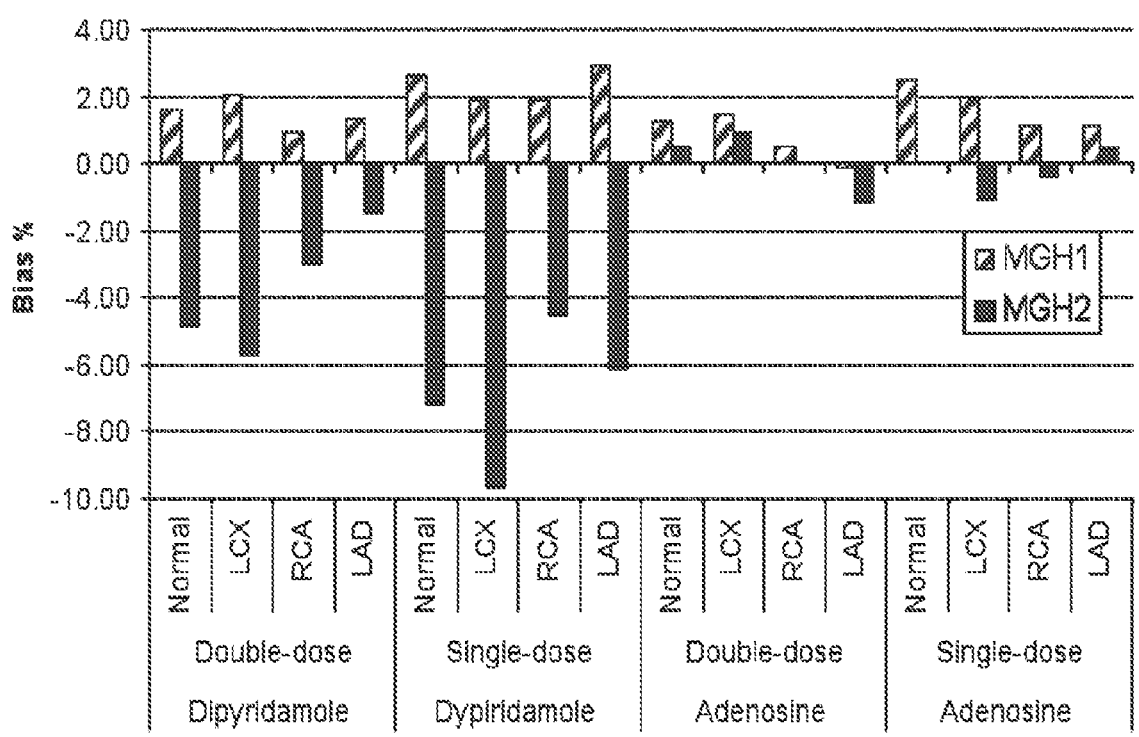
FIG. 4 is a bar graph that shows plots of the average bias calculated from the MBF estimated with MGH1 and MGH2 models using the MBF from the stress-only as reference. The mean bias is computed by pooling the same region over the subjects.
Figure 5:
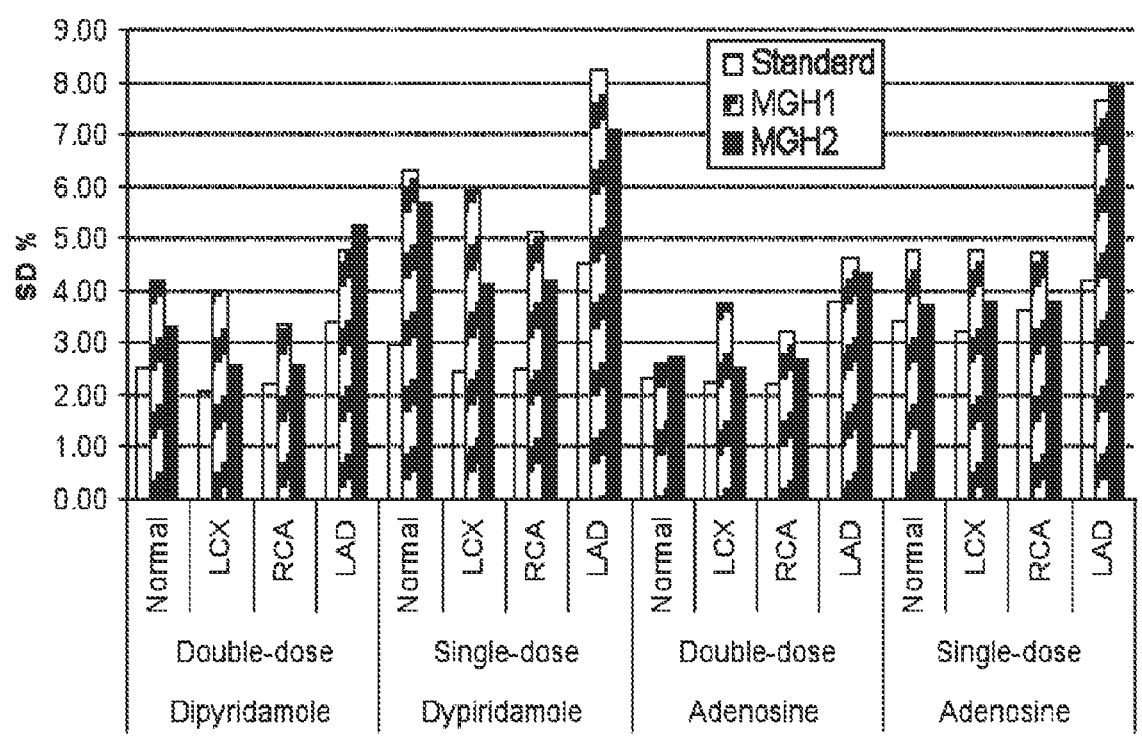
FIG. 5 is a bar graph that shows plots of the average standard deviation calculated from the MBF estimated with MGH1 and MGH2 models using the MBF from the stress-only as reference. The mean standard deviation is computed by pooling the same region over the subjects.

The comparison of bias and variance of MBF estimation from each model is presented in FIGS. 4 and 5. FIG. 4 shows the bias averaged over the subjects for each region. MGH1 is found to be nearly unbiased, with bias between −1% and 3%. No significant pattern of bias dependency on the myocardial sector was observed. In general, a higher tracer dose for the stress study reduces the bias for MGH1 method. On the other hand, MGH2 has a higher bias than the MGH1 method. For dipyridamole, an underestimation of MBF is found in all regions with bias ranging between −1% and −10%. Higher bias is observed in the single-dose stress studies. When adenosine is used as the vasodilator, the bias of MGH2 is fairly low, ranging between −2% and 2%. The average SD of the estimated MBF is shown in FIG. 5. The stress-only protocol, as the Standard method, has the lowest noise estimate, less than 5% in SD, for all the segments and conditions simulated. MBF estimates from MGH1 and MGH2 are of higher variance, ranging between 2% and 9%. Variance of the MGH1 and MGH2 estimates is reduced to less than 6% when double tracer dose is used for the stress study. In general, MGH2 has a lower SD than the MGH1 method.

Figure 6A:
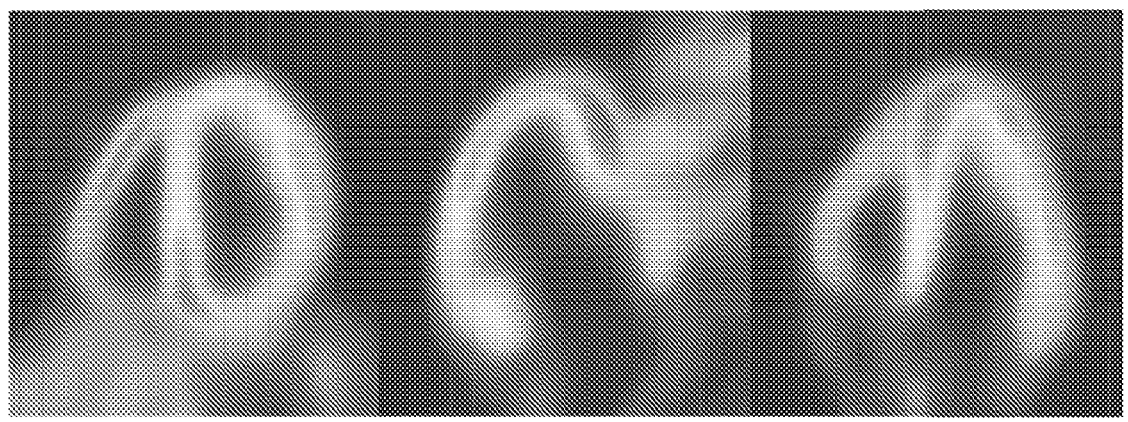
FIG. 6A provides a plurality of images and FIG. 6B is a polar map that graphically shows representative rest/stress $^{18}$F-Flurpiridaz PET study results.
Figure 6B:
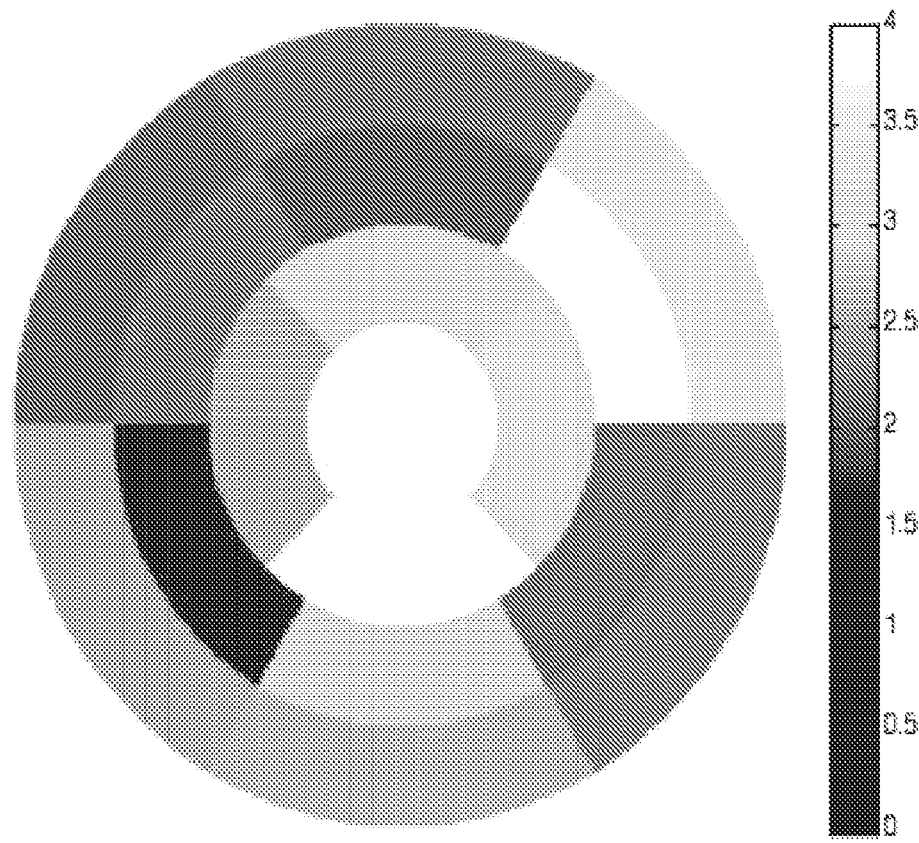

Finally, FIG. 6 shows a representative myocardial rest and stress study with the short axis, vertical and horizontal long axes with rest in gray scale and stress in color along with the corresponding coronary flow reserve (ratio of absolute myocardial blood flow at rest and during peak stress).

Considering first the "Standard" method, most contemporary quantitative methods assume that measurement of resting MBF can be described as a steady state condition and analyzed by compartment models with constant transport rates and rate constants. This is similar to the approach taken by Nekolla et al. who validated $^{18}$F-Flurpiridaz in animals by comparison with microsphere measurements. The analysis used in the present system and methods deviates from the conventional Standard method in that blood flow and flow-related rate constants are allowed to be time dependent in response to pharmacological stress. Based on prior research, different time-variation can be expected, depending on the detailed properties of the vasodilator. Previous work has not considered this effect and it should be taken into account, as not doing so may add to the bias and variability of measurements. The present system and methods parameterize a mathematically convenient functional form for F(t) so that estimating these parameters provides a summary description of the temporal flow variation. As a practical matter, adopting a more realistic mathematical function may lead to unidentifiable estimates of MBF. So, a carefully thought out trade off is required.

Another point to consider is the validation of flow measurements made during stress imaging. Microsphere flow estimates are considered to be the gold standard but the derivation of the microsphere flow equations also assumes constant flow. The assumption of constant flow enters the microsphere method through the Fick equation:

$$\int_0^T F(t)C_a(t)dt = F\int_0^T C_a(t)dt \quad \text{(Eq. 8)}$$

where F is the myocardial blood flow and $C_a(t)$ is the arterial concentration history of microspheres. This means that the accuracy of the microsphere method during stress imaging depends on the magnitude of the systematic error made by factoring the Fick equation.

There are a number of approaches to combined rest-stress imaging that have been considered. Among those are what can be called semiquantitative or ad hoc methods that use larger doses of radionuclide for stress imaging and neglect the effect of prior rest imaging entirely. "Subtraction" of rest images from stress images can improve contrast but it is not based on rigorous physiological and physical principles. More quantitative methods have been proposed in various reports. Kim et al. proposed (Kim, K. M., et al., J. Nucl. Med. 51, 1624-1631, 2010) and Iida et al. implemented (Iida, H., et al., J. Nucl. Med. 51, 1624-1631, 2010) a related model and measurement protocol for measuring the change in cerebral blood flow elicited with pharmacologic challenge. The Rust model is most relevant to imaging with $^{18}$F-labled MBF tracers (Rust, T. C., et al., Phys. Med. Biol. 51, 5347-5362, 2006). The Rust kinetic model predicts that the activity measured during the stress exam is the sum of the residual rest activity plus the new activity injected during pharmacological stress. Using the kinetic parameters estimated from fitting the rest images, the Rust model predicts the residual contributions to the stress images. Rust et al. assume that MBF is constant during stress imaging but also mention that "kinetic parameters would not be constant due to the infusion of adenosine during the scan" as a limitation of their model.

With respect to the present system and methods, the feasibility of absolute quantification of rest/stress MBF within a single, short imaging session was re-examined. Unlike previous methods, free tracer molecules were assumed to "feel" the effects of stress as a change in state whether they be part of residual activity from a previous injection, or "newer" molecules injected during infusion of a pharmacological stressor. In effect, once pharmacologic stress is started, the system is assumed to have no memory of the previous state. This key insight allows for treatment of the entire rest-stress measurement as a single study with a single input function that includes the contributions from both the rest and stress tracer injections. Transport and rate constants describing the inflow and egress of unreacted tracer molecules become time dependent and the equations no longer describe a classical compartment system.

Since, a priori, the functional form of the time dependence is not known, it is necessary to assume a convenient functional form for the fluxes and rate constants. Both a piecewise linear (MGH1 method) and a simpler two state formulation (MGH2 method) are described and evaluated by the simulation. Despite the more general and realistic assumptions the new method is not significantly more complicated than more conventional analyses.

In one example, a long rest study obtained with $^{18}$F-Flurpiridaz was analyzed. The first few minutes of the dynamic sequence were shown to be insensitive to the mechanisms that account for the long residence time of Flurpiridaz. In terms of compartment modeling, FIG. 2 shows that estimates of MBF reach a high precision, requiring only a few minutes of data, while being insensitive to physiologically plausible values of $k_3$. This means that binding of Flurpiridaz can be treated as a nominal effect which does not vary from subject to subject. From FIG. 2, it can be concluded that estimates of MBF with low bias and good statistical precision can be obtained in less than 10 min. Therefore, it is generally not necessary to prolong the rest study and pharmacological stress infusion can begin promptly, allowing for a shorter study design.

While the finding that only a few minutes are needed to obtain quantitative measurements of resting flow is of basic importance, there are other important questions to answer about combined rest/stress. These questions have to do with (1) whether it is possible to obtain accurate and precise MBF with a rapid single-scan rest/stress protocols under plausible physiologic assumptions, and (2) what the trade-off is between accuracy and signal-to-noise ratio due to overlapping rest and stress studies. Considering the Standard method with completely separate rest and stress measurement to be method of lowest radiation dose, another question relates to the level of activity required to obtain a signal-to-noise ratio similar to the MGH protocols. In one aspect, these questions can be answered by realistic Monte Carlo simulations based on a digital torso phantom with an anthropomorphic cardiac geometry. By following millions of photon histories, an ensemble of simulated dynamic studies was constructed with both normal and abnormal myocardial segments. Ensembles of data emulating the Standard method and the MGH1 method were simulated. The myocardial time-activity curves from simulated data were fitted to the Standard method, the MGH1 and MGH2 methods. The following properties of these three methods were found by evaluating the bias and precision performance. First, the Standard method produced the most precise estimates for the peak MBF during stress. This is because, in the Standard method, rest and stress studies are performed separately, so there is no mixture of the activity from the two tracer injections. This results in a simple and straightforward parameter estimation strategy, which provides the best precision. Second, combining a rest and stress study results in an increase in the parameter variance. For both MGH1 and MGH2, the activity after the onset of vasodilator infusion is affected by the time-dependence of $K_1$ and $k_2$. Furthermore, the model becomes more complicated than the Standard method and since the measured activity comes from two injections, the parameter variance will be increased for both MGH1 and MGH2. Therefore, choosing between the Standard method and the MGH methods becomes a trade-off between the study complexity, injected dose and the parameter precision. Considering all these factors, we believe that the convenience of a single scan session will outweigh the minor increase in the variance of MBF.

Based on the current simulations, the MGH method can be a useful tool for rest/stress studies. By examining the performance of the MGH1 method, the MBF bias was found to be small (<3%). As previously mentioned, the MGH1 method has a higher variance than the Standard method, but this increase of variance is modest as shown in FIG. 5. The standard deviation of MBF is less than 5% for double-dose and less than 9% for single-dose stress. The Standard method requires that the subject be repositioned for the rest study; whereas the MGH method offers a short, single-scan session protocol.

There are two variants of the MGH method. In one aspect, the MGH1 method is more accurate due to the more detailed model of the effects of vasodilators. However, the MGH2 method, as a simplified version of MGH1, also produced reasonable performance. By modeling the transition of MBF as a step change, fewer parameters need to be estimated for MGH2. As a result, MGH2 can be more precise than MGH1. However, since the approximation of the step change does not fully describe the kinetic behavior of MBF, MGH2 can be more biased than the MGH1 method. This is particularly obvious in the case as dipyridamole, as it takes longer (6.5 min) to reach the peak hyperemia than does adenosine (1.5 min). In other words, the MBF change in the MGH2 model can better approximate the fast transition in adenosine than dipyridamole. As a result, the MGH2 method can be more appropriate for fast-acting vasodilators as the accuracy of the MGH2 method is more dependent on the functional form of the time-dependent kinetics.

Compared to the Rust method, the MGH method is different in several important features: First, residual tracer molecules in plasma and myocardium are transported according to flow conditions which prevail during stress. Second, flow and clearance was modeled as a continuous function during stress imaging to account for the effect of the vasodilator. The modeling is the same whether the tracer molecule was introduced at rest or during vasodilation. Because the residual activity of the rest study is more properly modeled, a lower bias was expected. Third, the input function of the tracer is treated as a single entity in the MGH method while the Rust method requires the input functions from the two injections to be separated and extrapolated. In the current system and methods, a judgment on the performance of the Rust method was bit made as the simulated data are based on the $K_1$ and $k_2$ kinetics described by the MGH1 model. The MGH1 model is an approximation and can be further validated with animal or human data. The bias/precision performance of the Rust and MGH methods can benefit from further validation with real experimental data against reference MBF measured with microspheres.

Although this work is aimed toward application of $^{18}$F-Flurpiridaz, the modeling approach is general and can be applied to other tracers with relatively long half-lives such as $^{13}$N-ammonia. The model may also be applied for vasodilators other than the adenosine and dipyridamole or even exercise stress studies that can be performed with a patient under the fixed bed position within the scanner.

The system and methods described, in one embodiment, contemplate the use of an in vivo assay to measure MBF. While specific examples are provided, it is contemplated that a general implementation will include the use of an suitable PET tracer molecule that is compatible with one or more of a variety of medical imaging technologies. For example, in one embodiment, a method includes the steps of administering the tracer $^{18}$F-Flurpiridaz for PET imaging. However, the tracer molecule may not be used as a positron emitter, and instead may be designed to emit a different type of radiation or even display no radioactivity at all. Similarly, the tracer molecule may not be used for PET imaging, but rather be compatible with magnetic resonance imaging (MRI), ultrasound imaging, or any other type of suitable imaging technology.

Figure 7:
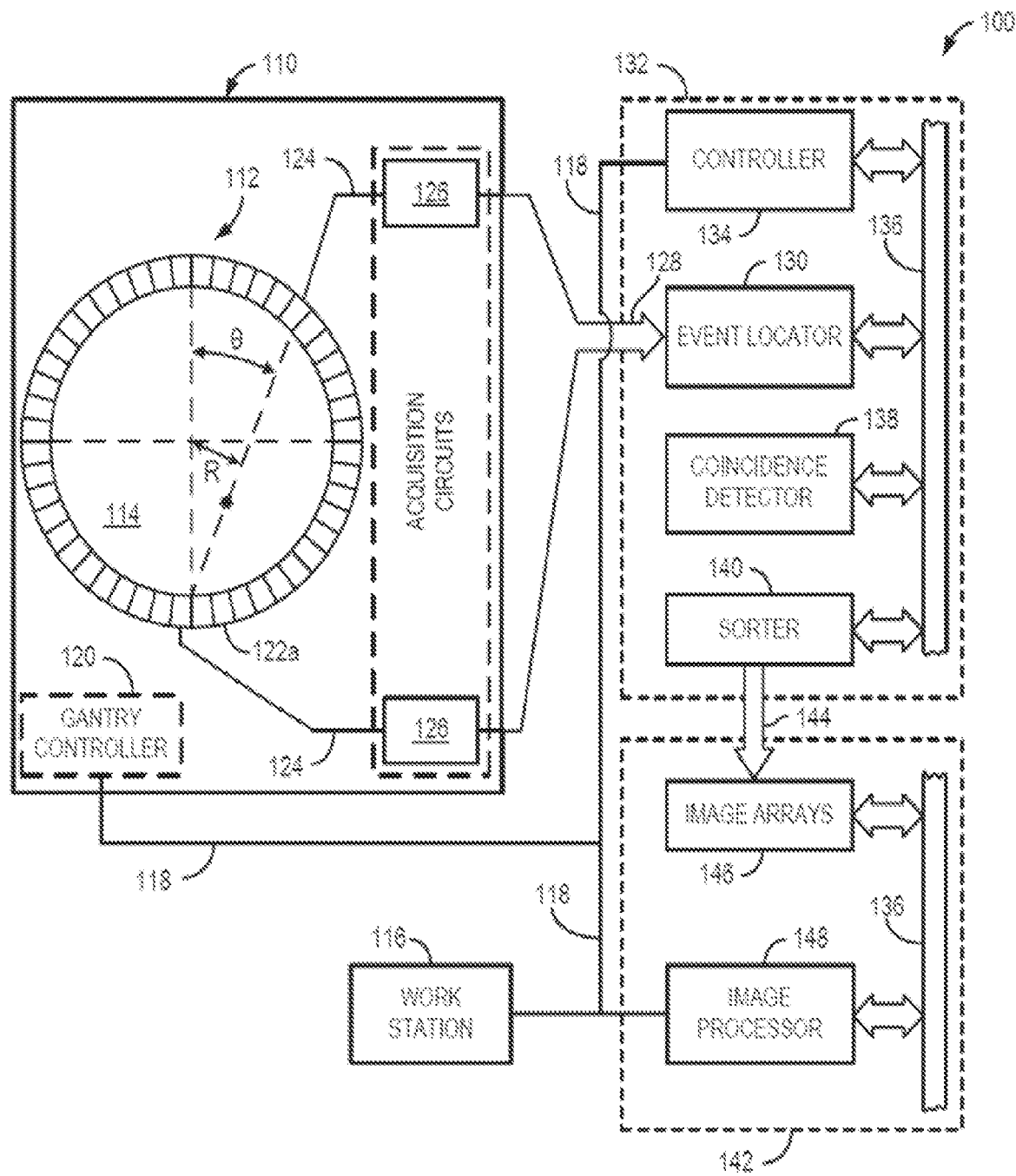
FIG. 7 is a schematic diagram of an emission tomography system in accordance with the present invention.

Referring to FIG. 7, a PET system 100 in accordance with the present invention includes an imaging hardware system 110 that includes a detector ring assembly 112 about a central axis, or bore 114. An operator work station 116 including a commercially-available processor running a commercially-available operating system communicates through a communications link 118 with a gantry controller 120 to control operation of the imaging hardware system 110.

The detector ring assembly 112 is formed of a multitude of radiation detector unit 122 that produces a signal responsive to detection of a photon on communications line 124 when an event occurs. A set of acquisition circuits 126 receive the signals and produce signals indicating the event coordinates (x, y) and the total energy associated with the photons that caused the event. These signals are sent through a cable 128 to an event locator circuit 130. Each acquisition circuit 126 also produces an event detection pulse that indicates the exact moment the interaction took place. Other systems utilize sophisticated digital electronics that can also obtain this information regarding the precise instant in which the event occurred from the same signals used to obtain energy and event coordinates.

The event locator circuits 130 in some implementations, form part of a data acquisition processing system 132 that periodically samples the signals produced by the acquisition circuits 126. The data acquisition processing system 132 includes a general controller 134 that controls communications on a backplane bus 136 and on the general communications network 118. The event locator circuits 130 assemble the information regarding each valid event into a set of numbers that indicate precisely when the event took place and the position in which the event was detected. This event data packet is conveyed to a coincidence detector 138 that is also part of the data acquisition processing system 132.

The coincidence detector 138 accepts the event data packets from the event locator circuit 130 and determines if any two of them are in coincidence. Coincidence is determined by a number of factors. First, the time markers in each event data packet must be within a predetermined time window, for example, 0.5 nanoseconds or even down to picoseconds. Second, the locations indicated by the two event data packets must lie on a straight line that passes through the field of view in the scanner bore 114. Events that cannot be paired are discarded from consideration by the coincidence detector 138, but coincident event pairs are located and recorded as a coincidence data packet. The coincidence data packets are provided to a sorter 140. The function of the sorter in many traditional PET imaging systems is to receive the coincidence data packets and generate memory addresses from the coincidence data packets for the efficient storage of the coincidence data. In that context, the set of all projection rays that point in the same direction (θ) and pass through the scanner's field of view (FOV) is a complete projection, or "view". The distance (R) between a particular projection ray and the center of the FOV locates that projection ray within the FOV. The sorter 140 counts all of the events that occur on a given projection ray (R, θ) during the scan by sorting out the coincidence data packets that indicate an event at the two detectors lying on this projection ray. The coincidence counts are organized, for example, as a set of two-dimensional arrays, one for each axial image plane, and each having as one of its dimensions the projection angle θ and the other dimension the distance R. This θ by R map of the measured events is call a histogram or, more commonly, a sinogram array. It is these sinograms that are processed to reconstruct images that indicate the number of events that took place at each image pixel location during the scan. The sorter 140 counts all events occurring along each projection ray (R, θ) and organizes them into an image data array.

The sorter 140 provides image datasets to an image processing/reconstruction system 142, for example, by way of a communications link 144 to be stored in an image array 146. The image arrays 146 hold the respective datasets for access by an image processor 148 that reconstructs images. The image processing/reconstruction system 142 may communicate with and/or be integrated with the work station 116 or other remote work stations.

Figure 8:
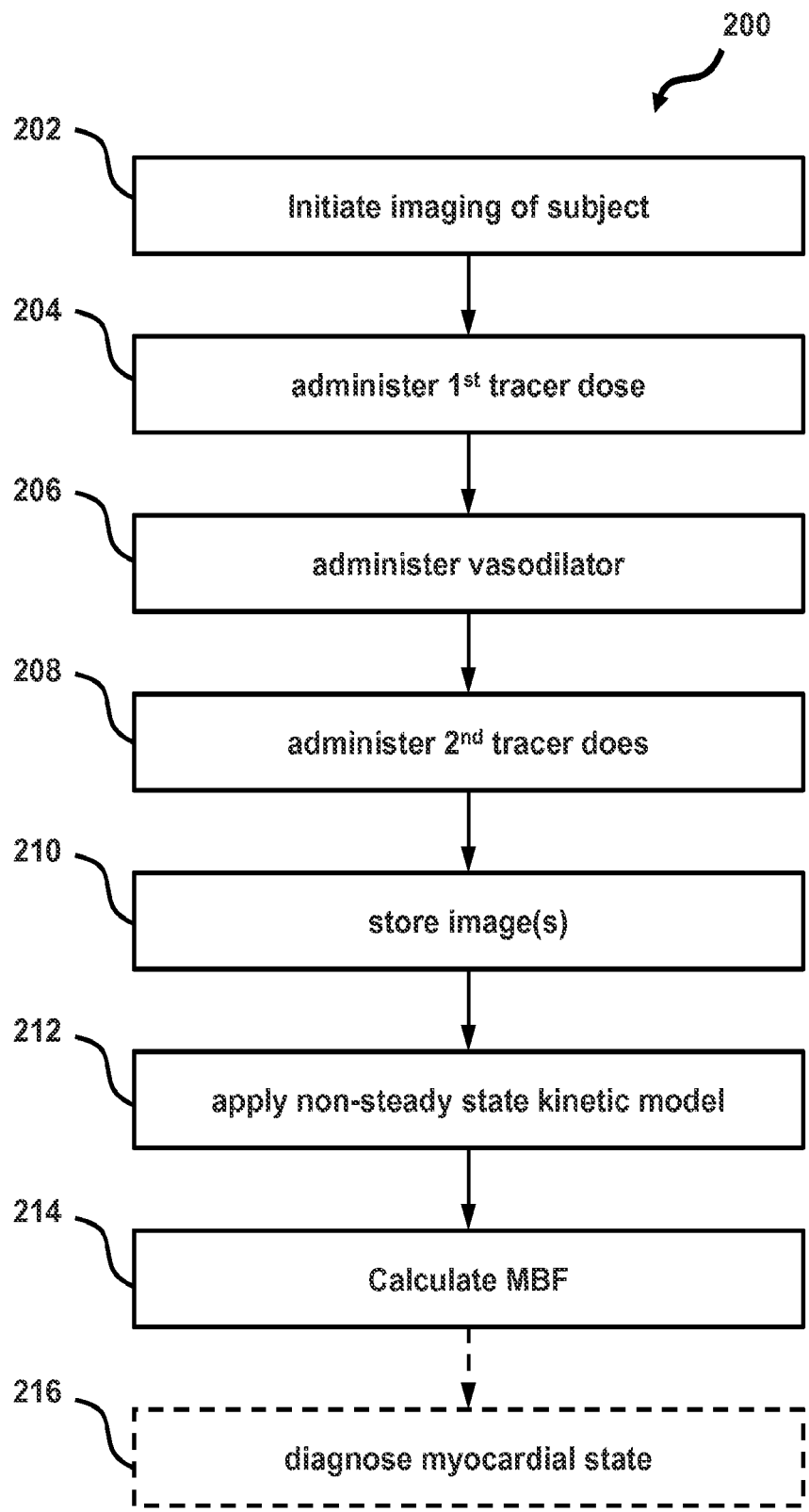
FIG. 8 is a flow chart setting forth the steps of an example of a method of using an emission tomography system in accordance with the present invention.

Referring to FIG. 8, a flow chart is provided that sets forth the steps of an example of a method 200 of using an emission tomography system in accordance with the present invention. In a first step 202 of the method 200, the subject is imaged using an emission tomography system such as a PET system. The subject is imaged for a period of time based on the kinetics of the at least two tracer doses to be administered. For example, when the tracer is $^{18}$F-Flurpiridaz, the subject can be imaged of the course of about 20 to about 30 minutes for the calculation of MBF. However, if it is desirable to calculate other physiological results, then the subject can be imaged for a longer overall time frame or beginning at a later time beginning with or at a later point after the step of administering a first dose.

In a next step 204 of method 200, a first dose of a tracer molecule, such as an $^{18}$F-based tracer molecule, is administered. One example of an $^{18}$F-based tracer is the PET tracer $^{18}$F-Flurpiridaz. The dose is, in one aspect, administered to a subject such as a human patient. During step 204, imaging of the subject continues, for example, to measure tracer activity associated with a rest state of the subject.

In a next step 206 of the method 200, a vasodilator is administered to the subject. In one aspect, the purpose of the vasodilator is to transition the state of the subject to a stress state. Accordingly, the vasodilator may be substituted for another compound or means of inducing a stress state in the subject. As in step 204, imaging of the subject continues in step 206, for example, to measure tracer activity associated with a transition from a rest state to s stress state of the subject.

In a next step 208 of method 200, a second dose of a tracer molecule, such as an $^{18}$F-based tracer molecule, is administered. In some aspects, step 208 can be similar to step 204. However, it is possible that the amount of the dose and/or the type of the tracer administered can vary. For example, a larger dose of the same tracer administered in step 204 can be administered in step 208. During step 208, imaging of the subject continues, for example, to measure tracer activity associated with a stress state of the subject.

In a next step 210 of method 200, the one or more images of the subject acquired with the emission tomography system can be stored in a non-transitory computer readable media. Then, in a step 212 of method 200, the one or more images can be analyzed, for example, with a computer processor. The analysis step can include the application of a kinetic model to the acquired image data. One example of a suitable kinetic model is a non-steady state, two compartment model as described herein. Following analysis, in step 214, one or more calculations can be made. The calculations can include quantification of subject perfusion and MC-I expression levels. Furthermore, in optional step 216 of method 200, the subject myocardium can be diagnosed as hibernating myocardium, healthy myocardium and/or ischemic myocardium.

With respect to steps 210 and 212, the images acquired with the emission tomography system and the program for application of the kinetic model can be stored in non-transitory computer readable media associated with one or more computer processing systems. For example, PET data can be acquired with and stored on one computer system, while the PET data can be analyzed with the kinetic model a separate computer system. The one or more computer systems can further be linked by way a wired or wireless connection for the transfer of data between the one ore more computer systems.

With reference to the above method 200, it is possible that implement the steps in the order shown or in any order suitable to the successful execution of the method 200. For example, imaging of the subject in step 202 may be carried out prior to and concurrent with administration of the doses in any of steps 204, 206 and 208. In another example, the step 212 of analysis can be intermittent with imaging over the course of method 200. While a number of examples have been described, other useful combinations of the steps of method 200 are both likely and anticipated.

Advanced Modeling Approach

While in a first aspect of the present invention, a specific, non-steady state, two compartment model was developed for rest-stress cardiac PET imaging, a second aspect of the present invention relates to further advanced modeling approaches. In one aspect, important innovations for measurement of myocardial blood flow are provided including: (i) direct parametric reconstruction (DPR) of MBF kinetic parameters from listmode projection data, and (ii) a strategy for estimating both rest and stress myocardial blood flow in a single scan session (concurrent rest-stress).

The present methodology reduces the variance of kinetic parameter estimates by estimation directly from listmode projection data. The reduction of parameter variance can include more accurate estimates of the noise (Poisson) available for the projection data than are available in the image domain, and temporal regularization provided within the DPR process via the kinetic model. This method acts on listmode rather than sinogram data, preserving the high temporal resolution of the raw PET data, and includes quantitative corrections for attenuation, detector sensitivity, scatter and random coincidences so as to yield un-biased estimates of the parametric maps. In general, DPR benefits from a prior standard reconstruction of the concentration data. The standard reconstruction may be used to estimate the input function, to define a valid kinetic region of interest definition (KRI) of regions suitable for analysis, and/or to provide information about the kinetics of regions that are not suitable for analysis with the kinetic mode. Direct parametric reconstruction (DPR) is then performed only in the KRI rather than in the whole image, which allows for a reduction in the computation time while generally reducing or eliminating the need to fit pixels outside the KRI. To keep the projection operation un-biased, it is possible to use the observed TACs of pixels lying outside the kinetic region of interest (KRI), which are known from the initial reconstruction step, and model the time-course of pixels located inside the KRI using the kinetic model. One advantage of this technique is that, by reducing noise in the estimation of the parametric map, it allows a broader range of trade offs between the injected dose of radioactivity and the precision of the parametric map. The present direct reconstruction, listmode framework also allows incorporation of additional information (such as the energy of individual photons and time-of-flight information) in the estimation process, a feature that can further improve the quantitative accuracy of kinetic parameter estimation. It has been demonstrated that a significant reduction of at least 3-6 fold in bias and variance of kinetic parameters estimates can be achieved with our proposed methods (Bias±variance improved from 85±181% to 11±57%). Furthermore, it has been shown that variance associated with the presently provided direct estimation of kinetic parameters approach was generally unaffected when dose was reduced from 4 to 0.3 mCi unlike traditional kinetic estimation methods from reconstructed frames.

Parametric images of cardiac function were estimated for concurrent rest-stress studies that preclude the need for separate rest and stress imaging sessions while reducing artifacts related to differences in patient positioning and condition as well as attenuation paths on different imaging visits. In one example, the patient is injected at rest, and again 10-15 min later during pharmacologic stress before the first injection has washed out/decayed. Previous methods attempting to achieve rest-stress within a short delay have been based on the incorrect approximation that a concurrent scheme is simply a summation of sequential rest-stress studies. The provided concurrent rest-stress kinetic model, on the other hand, has been shown to describe the tracer uptake in a comprehensive and rigorous way that allows the flow parameters to be time-dependent and results in equations with a simple interpretation. In one aspect, accurate simultaneous estimation of rest and stress kinetic parameters in concurrent rest-stress was confirmed. No statistically significant difference between the kinetic parameters estimated during concurrent and sequential rest-stress was observed.

In certain embodiments, the provided system an methods includes several components. A first component analyzes the mechanisms that affect transport of an $^{18}$F-flow tracer such as $^{18}$F-Flurpiridaz, and devises a novel strategy for sequential as well as simultaneous measurement of rest-stress parametric flow maps in a single ~30 min. scan session. In one aspect, the first component can enable a fully automated quantitation of MBF based on reconstructed concentration data using non-invasive computation of the left and right ventricle input functions using generalized factor analysis (GFADS) and dynamic orthogonal grouping (DOG) to increase SNR (expected factor 2-3) in the parametric images without compromising quantitative accuracy.

A second component can include direct parametric reconstruction (DPR) of the listmode data stream to compute the rest-stress flow maps with significantly lower parameter variance. In some aspects, the component can enable the ability to include the routine corrections for attenuation, scatter and random coincidences and b) the ability to segment the reconstruction volume into different regions, those in which the kinetic model is valid and others where the concentration histories will be used without modeling. In some examples, DPR Another embodiment of the present system and methods relates to the development and evaluation of two novel approaches for estimation of kinetic parameters. In one aspect, an automated kinetic modeling approach is developed to estimate flow parameters from dynamic reconstructed PET. In one aspect, a strategy is provided to quantify local MBF using partially trapped tracers such as $^{18}$F-Flurpiridaz. In one example, the strategy uses IV injection and PET listmode acquisition. The listmode data are integrated into time epochs (frames) such that the early frames are acquired at higher temporal frequency, when the concentrations are changing rapidly; whereas, later frames are integrated for a longer period, when the concentrations are changing more slowly. Presently, parametric cardiac imaging is performed on reconstructed dynamic PET frames using voxel-by-voxel (or ROI) kinetic analysis. This requires manual definition of the cardiac blood pool as left and right ventricular ROIs and produces moderately accurate parametric flow maps, with poor SNR. In contrast, the provided approach has been demonstrated to be fully automated, with non-invasive estimation of the right and left ventricle input functions, as well as accurate estimation of the kinetic parameters from reconstructed volumes or listmode projection data yielding accurate results that are robust to noise and very reproducible.

Figure 9:
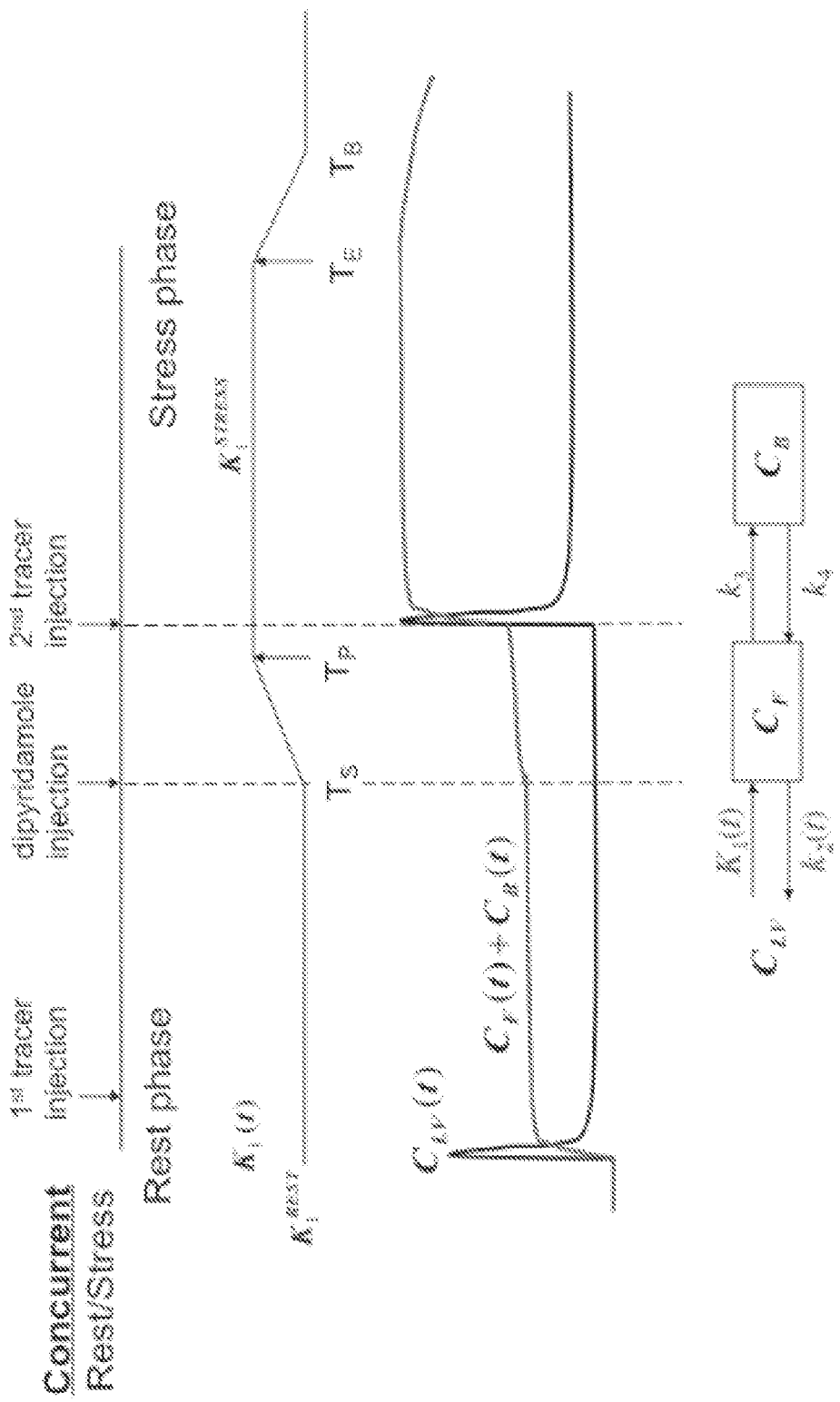
FIG. 9 is a graphic illustration of a proposed study protocol in accordance with the present invention and showing transition of the kinetic parameters and the time activity curves in LV and myocardium. Due to the effect of dipyridamole, MBF ($K_1(t)$) undergoes transitional changes before reaching the peak flow ($K_1(t)$ therefore is a variable with time). Kinetic parameters of $K_1$~$k_4$ can be estimated by fitting the whole time-activity curves to the model. In one aspect, there is no need to separate the activity residual of the rest study from the stress study. $T_s$ and $T_e$ denote the start and end of vasodilator infusion. Peak stress is reached at $T_p$, while MBF return to normal at $T_b$.

In another aspect, a flow measurement strategy incorporates knowledge of the basic properties of partially trapped tracers with a two-tissue compartment model, allowing simplifications appropriate to quantitative flow measurements. The full kinetic model is shown in FIG. 9. In this model the tracer can be in one of two states, either free, as the injected molecule, or bound to a receptor. In the example case of $^{18}$F-Flurpiridaz, previous studies have shown that it binds to the mitochondrial complex I. The product of plasma concentration ($C_p$) and transport rate $K_1$ is the force driving tracer from capillary plasma to the free space. Symbolically, $K_1$ is the plasmato-tissue transport rate, FE, the product of flow F and the unidirectional capillary extraction fraction, E. $k_2$ is a rate constant summarizing the egress from tissue to plasma. The rate constants $k_3$ and $k_4$ provide a summary description of binding and release of tracer. The full operational equation for the two compartment model is well known. In one aspect a focus is directed to the first few minutes after IV injection. First, it has been demonstrated that $K_1$ is an applicable approximation to blood flow since the unidirectional extraction fraction is greater than 90% at all physiological flow rates. Second, the ratio $k_3/(k_2+k_3)$, is between 0.2-0.6, meaning that after the first few minutes of scanning, about half the tracer entering the tissue space is bound and the effect of binding must be considered when interpreting the data. Third, it has been shown that at least an hour of scanning is required to obtain good estimates of all parameters. Fourth, the data have shown that by restricting the scan period to about 5 minutes duration, the model analysis can be simplified and blood flow ($K_1$) estimated with good accuracy and higher SNR. Conversely, the ability can be lost to measure the other parameters.

Figure 14A:
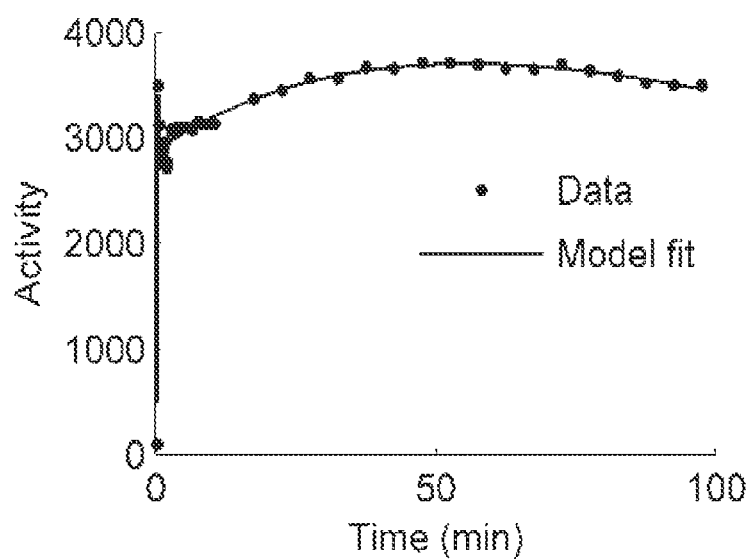
FIGS. 14A-14C are a series of graphs that show data from a monkey study.
Figure 14B:
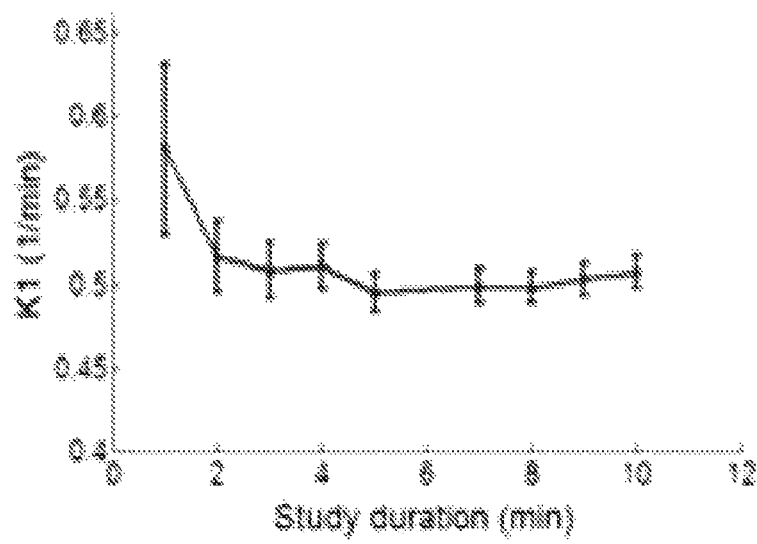
Figure 14C:
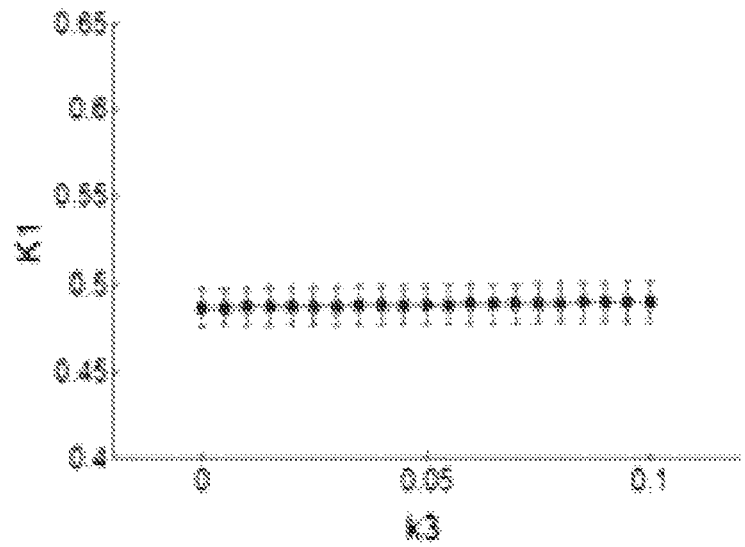

In one example, a simplified approach, suitable for analyzing the first 5-10 minutes of scanning, either a sequential rest or stress measurement, is to fix $k_3$ to a nominal value and set $k_4=0$ (i.e. to assume the release of bound tracer is negligible during the scan period). The simplified operational equation is Eq. 9:

$$C_T(t) \approx \left(\varphi_{lv} + \frac{V_{wb}}{V_t}\right)C_{lv}(t) + \varphi_{rv}C_{rv}(t) + \qquad \text{(Eq. 9)}$$
$$K_1 \cdot C_P(t) \otimes e^{-(k_2+k_3)t} + K_1 \cdot k_3 \int_0^t e^{-(k_2+k_3)\mu} du \cdot d\mu$$

where $C_T(t)$ is the instantaneous tissue concentration, $\varphi$ is the spillover fraction of left or right ventricle (subscript lv or rv), $V_{wb}/V_T$ is tissue blood volume, $C_{lv}(t)$ and $C_{rv}(t)$ are the concentration histories for the left and right ventricle, respectively, $K_1$ is the flow extraction product, $C_p(t)$ is the plasma concentration history. Referring to FIGS. 14A-14C, the data show that for the first 10 minutes, the flow estimate is insensitive to the values of $k_3$ and $k_4$. There are four parameters to estimate in the operational equation:

$$\left(\varphi_{lv} + \frac{V_{wb}}{V_t}\right), \quad (1)$$

$$\varphi_{rv}, \quad (2)$$

$$K_1, \quad (3)$$

$$k_2. \quad (4)$$

Results obtained in realistic Monte Carlo cardiac simulations and cynomolgus monkey studies show that $K_1$ can be estimated with low bias and high precision with 5 minutes of scanning.

Generalized Factor Analysis of Dynamic sequences (GFADS) is a powerful approach that allows for extraction of temporal data (i.e., time activity curves), and the corresponding spatial distributions (i.e., factor images), from a series dynamic images (13. El Fakhri, G., et al., *J Nucl Med*, 2000. 41: p. 1400-1408; El Fakhri, G., et al., *Med Phys*, 2006. 33: p. 1016-1024). This approach has many advantages over ROI-based approaches that include automation, robustness to noise (estimation of TAC from all voxels instead of an ROI) and reproducibility. A dynamic sequence of N PET frames can be represented by an M×N matrix A, where M is the number of voxels in a dynamic PET study. The observed data is described as a linear combination of factors F, where the coefficients of the combination are defined in C:

$$A_{mi} = \sum_{p=1}^{P} C_{mp} F_{pi} + n \quad \text{(Eq. 10)}$$

F contains P factors and n denotes noise in the data, yielding (N−P)M degrees of freedom in the model. The factor curves, F, define the time course of the factors whose spatial definition is contained in matrix C (factor image). In order to solve (Eq. 10), the number of factors P must be known a priori. Estimation of the factors F and factor images C is based on minimization of:

$$f_{PLS}(C, F) = \sum_{m=1}^{M}\sum_{i=1}^{N}\left(A_{mi} - \sum_{p=1}^{P} C_{mp} F_{pi}\right)^2 + \alpha\left[\sum_{m=1}^{M}\sum_{p=1}^{P} H(C_{mp}) + \sum_{p=1}^{P}\sum_{i=1}^{N} H(F_{pi})\right] \quad \text{(Eq. 11)}$$

where $H(x)$ is equal to 0 for and equal to $x \geq 0$ for $x^2$ for $x < 0$, and $\alpha$ is a penalty coefficient that can be chosen from a wide range of values. The reproducibility and accuracy of the approach has been validated in more than 1000 clinical $^{82}$Rb and $^{13}$N-ammonia studies as well as in an acute ischemic canine model and microspheres (El Fakhri, G., et al., *J Nucl Med*, 2009. 50: p. 1062-1071; El Fakhri G., et al., *Circulation*. 2007, 116 (16): 717).

In another aspect, the system and methods can include a dynamic orthogonal grouping (DOG) approach. The estimation of kinetic parameters on a voxel-by-voxel basis yields very noisy parametric images due to high levels of noise in TAC derived from single voxels. Using a filtering approach reduces noise but results in a degradation of spatial resolution of the parametric images. In order to reduce noise without compromising spatial resolution, a DOG approach can be applied. The DOG approach has been applied to $^{82}$Rb-82 [Kimura, Y., et al., *Phys. Med. Biol.*, 1992. 47: p. 455-468) to perform 3D grouping of voxels with similar time course into several groups of size G (that we call macro-voxels). DOG consists of two steps: Step 1: An orthogonal analysis is performed in every dynamic voxel $TAC_i(t)$. The reduced-dimensional data subspace S that contains most of the data is a 3D subspace, consistent with the number of GFADS factors. The coordinates of each dynamic voxel in S are calculated as the product of the principal vectors with $TAC_i(t)$, i.e., 3D vectors $P(TAC_i(t))_\tau$ are obtained where $\tau = 1 \ldots 3$ describes the location of a given dynamic voxel $TAC_i(t)$ in the 3D data sub-space S, and P denotes the projection operator onto the $\tau^{th}$ base vector. Step 2: The grouping algorithm is applied to the 3D vectors $P(TAC_i(t))_\tau$. Euclidean distances are calculated between each two dynamic voxels and the dynamic voxel for which the sum of distances to all other voxels is highest is determined. Next, the G-1 closest dynamic voxels are found. These G dynamic voxels constitute the first group. The procedure is repeated until all dynamic voxels are grouped (El Fakhri, G., et al., I J Nucl Med, 2005. 46: p. 1264-1271). Finally, the estimated kinetic parameters are remapped onto a kinetic parametric volume.

Yet another aspect of the present system and methods includes development of a strategy for direct estimation of kinetic parameters from listmode projections. In conventional parametric imaging, kinetic parameters are estimated by fitting pixel-wise TACs which typically results in very noisy parametric maps. Direct reconstruction of kinetic parameters from projection data, (i.e., parametric reconstruction), can reduce noise in parametric images or, for a given noise level, reduce the injected dose. The noise reduction is due to 1) the fact that noise is better modeled in the projection domain (Poisson) than in the image domain (approximately Gaussian but difficult to estimate and 2) the use of temporal regularization within the reconstruction process provided by the kinetic model. Most existing DPR approaches require linearization of the kinetic model (e.g., using the Patlak method) and are therefore not general. Others have proposed methods for the direct estimation of one and two-compartment model kinetic parameters; however these have only been tested in simple scenarios on simulated data not accounting for attenuation, variable detector sensitivities and random and scatter coincidences. In one aspect of the present system and methods, four different methods were implemented, each having different computational requirements. A pixel and sinogram-wise DPR approach can be developed based on the EM (sinogram-wise), CG (sinogram-wise), SPR (pixel-wise) and PICD (pixel-wise) algorithms that are applicable in the clinic, (i.e. that are computationally feasible and account for attenuation, detector sensitivity, scatter and random effects). These DPR techniques can be adapted to listmode data since this format preserves the high temporal resolution of the dynamic raw data, reduces memory requirements and enables the use of TOF information in the DPR process.

Another aspect of the present system and methods includes listmode based direct parametric reconstruction (DPR). The log-likelihood function of dynamic listmode data is:

$$l = \sum_{n=1}^{N} \log\left[\sum_{i=1}^{M} a_{ni}F(t_n|\theta_i) + Sc_n(t_n) + R_n(t_n)\right] - \sum_{i=1}^{M} s_i \int_0^T F(t|\theta_i)dt \quad \text{(Eq. 12)}$$

where n is the coincidence index, N is the total number of coincidences, i is the image voxel index, M is the total number of voxels in the parametric image, $\theta_i$ is the vector of kinetic parameters for pixel i, $t_n$ is the time of arrival of coincidence n, $F(t|\theta)$ is the PET activity concentration for pixel i calculated using the kinetic model with vector of parameters $\theta$, $\alpha_{ni}$ is the primary system matrix element for coincidence n and image pixel i (containing attenuation and sensitivity correction factors), $s_i$ is the detection sensitivity of pixel i, T is the duration of the acquisition and $Sc_n(t)$ and $R_n(t)$ are the average number of scatter and random counts detected in time frame t and in the line of response (LOR) $X_n$. The gradient of Eq. 12 with respect to the parametric map $\theta_i$ is readily computed and depends on the current estimate of the parametric map and the derivative of the kinetic model F.

With respect to spatial regularization, the maximization of Eq. 12 with respect to the parametric maps is an ill-posed inverse problem. Regularization can be performed by adding a roughness penalty to Eq. 12, acting either on the parametric maps or the image TACs. The present approach is regularized in the image domain because 1) this allows comparison of its performance to that of the indirect approach (i.e., regularized image reconstruction+pixel-by-pixel TAC fitting) by regularizing it with the same roughness penalty and 2) this introduces only one regularization strength instead of N (where N is the number of parametric maps to be reconstructed).

With respect to initialization and input function, Eq. 12 is a non-convex function of the parametric maps, so that it is beneficial to start the estimation process using a judicious initial guess of the parametric maps, to ensure convergence toward its global maximum. The present system and methods use the standard reconstruction of the concentration data and GFADS to estimate the LV and RV concentration histories and the myocardial factor image to determine the KRI region for DPR. Since Eq. 9 is of the form: $C(t,\varphi_{lv}, \varphi_{rv},K_1,k_2)=\varphi_{lv}\cdot C_{lv}(t)+\varphi_{rv}\cdot C_{rv}(t)+K_1\cdot q(t,k_2)$ where the $\varphi_{rv}$, $\varphi_{lv}$, and $K_1$ enter as linear parameters and q is a known function. A good initial guess can be formed with the following procedure: 1) Tabulate $q(t,k_2)$ for a mesh of $k_2$ values. 2) For each $k_2$ in the table, find the least squares solution for the linear parameters. 3) Choose the solution for which the sum of squares is a minimum. In one example, median filtering is used to reduce noise of the estimates of the parameters.

To address DPR within a KRI, instead of maximizing Eq. 12 with respect to all pixel kinetic parameters, the present approach maximizes it, in one aspect, only with respect to pixels lying within the mask of the myocardium (this mask may be obtained by masking the myocardium image factor obtained with GFADS) and that are known to follow the kinetic model F. This strategy will, in some aspects: 1) reduce computation time as it reduces the number of parameters to estimate from a few millions to a few thousands and 2) reduces the bias in the estimation of the kinetic parameters in the myocardium by avoiding fitting the liver, lungs, bones, etc. TACs with the model F, which they might not follow. To correctly compute projections in the maximization of Eq. 12, the dynamic volume within the DPR process is estimated using reconstructed TACs for pixels lying outside of the volume of interest (VOI) (obtained in the initial estimation of the parametric maps) and using the kinetic model for pixels lying in the KRI. This strategy corresponds to replacing the projection operation in Eq. 12 by $\Sigma_{i \in VOI}\alpha_{ni}F(t_n|\theta_i)+\Sigma_{i \notin VOI}\alpha_{ni}\rho_i(t_n)$, where $\rho_i(t_n)$ is the reconstructed image at time $t_n$.

Considering quantitative corrections, to obtain low-bias parametric maps, it is prudent to incorporate estimates of the scatter and random coincidences in the projector of Eq. 12 (attenuation and detector sensitivity correction can be performed as usual in the system matrix). Note that although listmode DPR is frameless, in some aspects, it is necessary to define frames for the implementation of the scatter and random corrections since these are performed using estimated sinograms of the random and scatter coincidences. This step uses the same set of frames and the same sinograms of random and scatter coincidences as those used in the initial image reconstruction process in order to avoid estimating them twice. The random sinogram is estimated for every time frame using the singles approach since this technique is low-bias and very low-noise. The scatter sinogram is computed using the single scatter simulation (SSS) and is scaled to the data using tails fitting (TF). Instead of applying SSS frame-by-frame however, the present approach can enable application to a reduced number of frames followed by linear interpolation to estimate the scatter distribution in every time frame. The optimal number of scatter frames needed to yield low-bias estimation of the parametric maps can be determined as an aspect of the present system and methods.

Referring now to the choice of the maximization algorithm, several reconstruction algorithms can be used to maximize Eq. 12. Iterative schemes for maximizing Eq. 12 involving different DPR algorithms have been previously described. Example algorithms include relative performances of the conjugate gradient (CG, sinogram-wise), parametric iterative coordinate descent (PICD, pixel-wise) and surrogate parametric reconstruction (SPR, pixel-wise). Each of these algorithms can include a regularization term and quantitative corrections for attenuation, detector sensitivity, scatter and random coincidences and can be applied in a KRI rather than for all pixels as long as the TACs of pixels lying outside of the KMR are known. In order to reduce computation, one aspect of the present system and methods includes precomputing the system matrix used in these algorithms (instead of computing it on the fly as is often done in listmode reconstruction). One approach includes the use of pre-computed system matrix reconstruction strategies that have been developed for sinogram data to the reconstruction of listmode data.

Yet another aspect of the present system and methods includes objective assessment of the performance of kinetic modeling approaches in CAD related tasks. In one example, the performance of the methods described herein can be evaluated in simulated sequential rest and stress studies generated using realistic Monte Carlo simulations modeling the geometry of the patient and the PET scanner as well as scatter and random coincidences (Guerin, B. et al., *IEEE Nucl Sci*, 2008. 55(3): p. 942-952). Dynamic studies can be simulated by generating listmode files corresponding to dynamic structure (i.e., myocardium, myocardial defects, LV and RV, lungs, bones etc . . . ), generating random coincidences detection times according to the TACs of these dynamic structures and then combining the listmode files corresponding to each structure. The TACs used in these simulations can be obtained from patients imaged with tracers such as $^{18}$F- Flurpiridaz compound.

The performance of the present system and methods can be assessed in dynamic physical phantom acquisitions obtained by imaging the different compartments of a Data Spectrum cardiac phantom separately. Virtual dynamic cardiac studies can then be obtained by generating random arrival times of the coincidence in the listmode files corresponding to every compartment according to the same $^{18}$F-Flurpiridaz patient TACs than the ones used in the aforementioned Monte Carlo simulations.

Example methods, such as GFADS+DOG and DPR, can be evaluated against the standard approach of reconstructing a dynamic volume and then fitting the reconstructed TACs pixel-by-pixel. To ensure that this comparison is fair, all three approaches can be regularized using the same roughness penalty acting on TACs (rather than on parametric maps which could also be possible in DPR) and can be corrected for attenuation, detector sensitivity, scatter and random coincidences using the same correction factors. Each method can be assessed in terms of variance and bias of the parametric maps since the reference maps will be known in these Monte Carlo simulations and phantom acquisitions.

Next, the performance of the present methods can be assessed in activity estimation tasks related to CAD and compared to pixel-wise TAC fitting. In one aspect, activity distributions can be grouped based on severity and extent of modeled (simulated or acquired) ischemia to generate three conditions: normal, ischemic, scarred myocardium. Kinetic parameters can be then estimated in the myocardial defect for each "subject" and binary classification into groups performed by calculation of the likelihood of belonging to each group. Pairwise linear discrimination tasks can then be performed using, for example, estimation ROC analysis. Area under the ROC curve ($A_z$) will be used as the performance metric, and results compared to a standard.

Another embodiment of the present system and methods relates to extension and evaluation of the kinetic modeling methods to concurrent rest-stress PET. In a first aspect, simultaneous joint estimation of rest and stress kinetic parameters are developed from reconstructions. FIG. 9. illustrates the central concept that rest-stress measurement is considered to be a single study in which the blood flow is time dependent. Previous analytic approaches incorrectly attempted to correct the concentrations measured during stress by subtracting or extrapolating activity from the (first) rest injection (Rust, T. C., et al., Phys. Med. Biol., 2006. 51: p. 5347-5362). In one aspect, considering the rest-stress measurement to be a single study with two tracer injections and one composite input function allows for rigorous accounting of the residual "background" of tracer due to the first injection. Whatever residual activity remains from the first injection is naturally accounted for in the kinetic model.

In one example of the present system, the total rest-stress scan period is on the order of 20 to 30 minutes. Because of the short duration, in some embodiments, simplifying assumptions can be made regarding the kinetics of tracers such as $^{18}$F-Flurpiridaz. The assumptions can include that 1) the rate constants $k_3$, $k_4$ for $^{18}$F-Flurpiridaz and MC-I do not change over the experimental period; and 2) the release of bound tracer is very slow, allowing the return of bound tracer to the free pool to be neglected. The subject remains in the same position throughout the study. In some embodiments, there are at least two tracer injections, one when the subject is in the rest state and the other following an infusion of a vasodilator, such as dipyridamole.

In one example, during the first (rest) phase of the study the transport rates and fluxes are assumed to be constant; with the start of the vasodilator infusion, $K_1$ and $k_2$ are considered to be time dependent. The second tracer injection is made at the end of infusion, the time considered to be "peak" stress, when flow is expected to be maximal. Considering these assumptions, Eq. 9 can be modified to accommodate the time dependence, as in Eq. 13.

$$C_T(t) \approx \left(\varphi_{lv} + \frac{V_{wb}}{V_t}\right)C_{lv}(t) + \varphi_{rv}C_{rv}(t) + \qquad \text{(Eq. 13)}$$
$$e^{-\int_0^t (k_2(z)+k_3)dz} \cdot \int_0^t e^{\int_0^u (k_2(z)+k_3)dz} K_1(u)C_P(u)du +$$
$$k_3 \int_0^t e^{-\int_0^u (k_2(s)+k_3)ds} \int_0^\mu K_1(u)C_P(u)e^{\int_0^u (k_2(s)+k_3)ds} du \cdot d\mu$$

The two tracer injections are considered to yield a single input function. In one embodiment of the present methods, the four-dimensional PET data are analyzed with GFADS, yielding estimates of the left and right ventricular concentration history for the entire experimental period. In addition to estimating the parameters $$\left(\varphi_{lv} + \frac{V_{wb}}{V_t}\right),$$

$\varphi_{rv}$, $k_3$, some time dependence for $K_1(t)$ and $k_2(t)$ is assumed. Several different functional forms can be tested, such as 1) the basic hypothesis of instantaneous switch from rest flow to peak flow; and 2) a ramp change from rest to peak flow. There are also a number of details about the parameter estimation procedure: a stepwise estimation process can be useful. First, the rest parameters are estimated using weighted nonlinear least squares, assuming a nominal value for $k_3$. These estimates are used in a penalized least squares fit of the entire time course, including direct estimation of $k_3$ and peak stress flow.

The two models are then compared to simpler kinetic models such as the one previously proposed by Rust et al. These models (noted conventional model) assume that TAC from the concurrent rest/stress study is a summation of two independent studies. They do not account for the fact that the kinetic parameters are no longer the same during the pharmacological stress and can lead to significant bias of estimated MBF.

A further aspect of the present system and methods includes a direct estimate of rest and stress kinetic parameters from listmode data. The DPR method can be extended to the joint estimation of the stress and rest parametric maps in a single imaging session. The expected value of the concentration symbolized by $F(t,\theta)$ is replaced by operational equation Eq. 13. In one example, a step-wise joint estimation approach is used that parallels the conventional fitting process: First, rest data is used to estimate the maps of spillover coefficients for RV and LV as well as the $K_1$ and $k_2$ maps. Then the entire rest-stress period is fit with Eq. 13 while penalizing the spillover fractions and resting $K_1$, $k_2$.

Strategies exist to evaluate image based and projection based concurrent rest/stress kinetic parameter estimation techniques. For example, Monte Carlo simulations and phantom acquisitions can be extended to generate dynamic PET data for concurrent rest-stress studies. Metrics (e.g., area under the ROC) are used to compare the performance of the present image-based and projection-based approaches to that of the traditional strategy consisting in first reconstructing the dynamic volume and then fitting each pixel TAC independently.

EXAMPLE 1

Non-Steady State Modeling Approach

To evaluate and compare the methods proposed in this work, simulation studies were performed based on the kinetic parameters derived from human studies conducted with $^{18}$F-Flurpiridaz, formerly known as $^{18}$F-BMS747158-02 (Lantheus Medical Imaging, North Billerica, Mass.). As a pyridazinone analog, $^{18}$F-Flurpiridaz binds to the mitochondrial complex I with high affinity. The combination of high first pass extraction and complex I binding ensure a high uptake in the myocardium with long residence time, due to the high mitochondrial density in the myocardial wall. Data from a rat model have shown that $^{18}$F-Flurpiridaz has an extraction fraction of greater than 90% over the physiological MBF range, which makes it an attractive perfusion tracer. Validation of MBF measured with $^{18}$F-Flurpiridaz has been performed by Nekolla et al. in pigs by comparison to microsphere and $^{13}$N-ammonia flow measurements. Good agreement between the MBF from $^{18}$F-Flurpiridaz and microspheres has been demonstrated to exist for a wide range of blood flow values.

As an example case, kinetic analysis was carried out based on $^{18}$F-Flurpiridaz clinical data. $^{18}$F-Flurpiridaz data was used to determine the local myocardial kinetics used in the simulations. These data included three subjects who underwent rest and stress imaging. In these studies, rest and stress imaging sessions were separated by at least 2 h. First, the rest and stress studies for each of the subjects were analyzed separately. These data were fitted to the two-compartment tissue model, using methods similar to a previous study (Nekolla, S. G., et al., *Circulation* 119, 2333-2342, 2009). For each subject, the acquired stress images were first aligned to the images of the rest study using the nonrigid image registration tool from SPM8 9 Ashburner, J., et al., *Hum. Brain Mapp* 7, 254-266, 1999). The LV and RV input functions for each subject and each study were extracted with generalized factor analysis on dynamic series (GFADS) (El Fakhri, G., et al., *J. Nucl. Med.* 46, 1264-1271, 2005; El Fakhri, G., et al., *Med. Phys.* 33, 1016-1024, 2006). The LV input function was used to approximate the plasma input function. No metabolite correction was performed. Because there is a 2-h gap between the rest and stress studies, the residual myocardial activity from the first tracer is mostly tracer bound to MC1 and is nearly unaffected by the stressor. The rest and stress image volumes of the heart were segmented into 17 standard segments. Time-activity curves were calculated for each segment. The residual activity from the rest study was estimated and subtracted from the stress time-activity curve. Then, the kinetic parameters were estimated for each segment under the resting state with its 25-min time-activity curve. $k_3$ was fixed as 0.026 (1/min) during the curve fitting. For the time-activity curve of the stress study, only data within the first 7.5 min were used in the curve fitting. After the parameters were estimated for all 17 segments, the cardiac flow reserve (CFR=$K_{1,s}/K_{1,r}$) of each segment was calculated. For the left anterior descending (LAD) territory, the segments with the two lowest CRF values were selected and the mean of each kinetic parameter was calculated from the estimated parameters of those two segments. The same calculation was repeated for right coronary artery (RCA) and left circumflex (LCX) as well. After two segments were picked for each territory, the kinetic parameters of the other 11 segments were averaged to compute the average kinetic parameters of the normal myocardium. The computation of the kinetic parameters of the normal myocardium, LAD, LCX, and RCA territories was performed separately for each subject. Table 1 summarizes kinetic parameters $K_1$ and $k_2$ estimated from the clinical $^{18}$F-Flurpiridaz studies and used for Monte Carlo simulations.

TABLE 1

| Subject | Myocardium | Rest | | Stress | |
| --- | --- | --- | --- | --- | --- |
| | | $K_1$ | $k_2$ | $K_1$ | $k_2$ |
| 1 | Normal | 0.68 | 0.08 | 1.96 | 0.07 |
| | LAD | 0.56 | 0.07 | 1.04 | 0.05 |
| | RCA | 0.74 | 0.08 | 1.26 | 0.08 |
| | LCX | 0.58 | 0.08 | 0.99 | 0.05 |
| 2 | Normal | 0.74 | 0.11 | 2.29 | 0.12 |
| | LAD | 0.78 | 0.11 | 1.60 | 0.07 |
| | RCA | 0.68 | 0.08 | 1.43 | 0.11 |
| | LCX | 0.94 | 0.13 | 2.10 | 0.10 |
| 3 | Normal | 0.60 | 0.05 | 2.09 | 0.23 |
| | LAD | 0.64 | 0.04 | 1.58 | 0.18 |
| | RCA | 0.58 | 0.03 | 0.68 | 0.17 |
| | LCX | 0.69 | 0.05 | 1.61 | 0.24 |

Due to the relatively short measurements obtained in human studies, longer duration $^{18}$F-Flurpiridaz measurements were made in a healthy 4.1-kg cynomolgus monkey. The animal was imaged under resting state and general anesthesia with 1%-2% isoflurane mixed with 100% oxygen. A 100-min dynamic $^{18}$F-Flurpiridaz PET study, with 1.25 mCi injected dose, was acquired with a microPET P4 system from Concorde Microsystems, Inc. Images were reconstructed with filtered back-projection (FBP) into 24×5-s, 6×30-s, 5×60-s, and 18×300-s frames. The LV and RV input functions were extracted with GFADS. A region of interest was drawn over the myocardium and used to calculate the time-activity curve which was then fitted to the standard four parameter, two-compartment model, with corrections for blood-to-tissue spillover in Eq. (3). Compartment model kinetic analysis tool (COMKAT) (Muzic Jr., R. F., et al., *J. Nucl. Med.* 42, 636-645, 2001; Fang, Y. H., et al., *J. Nucl. Med.* 51, 77-84, 2010) under MATLAB R2009a (Mathworks, Natick Mass.) was used to perform the non-linear least squares for parameter estimation with the frame duration used as the statistical weight. After the kinetic parameters were estimated from the 100-min time-activity curve, the data were refit while progressively reducing the observation period. First, $K_1$, $k_2$,$f_1$, and $f_{RV}$ were estimated as a function of study duration of the time-activity curves, ranging from 1 to 10 min. Due to the short measurement periods used, $k_3$ and $k_4$ were fixed to the values estimated by the 100-min data. The parameter variance of each parameter was approximated by the covariance matrix from the non-linear least squares fitting. Then, the duration of the time-activity curve was fixed to 10 min and estimation of $K_1$, $k_2$, $f_1$, and $f_{RV}$ was repeated with $k_3$ fixed at values ranging from 0 to 0.1, incremented by 0.005. $k_4$ was fixed as the value derived from fitting the 100-min data. Again, variance of each estimated parameter was approximated by the covariance matrix.

To provide an initial evaluation of the proposed new single-session rest/stress measurement strategy and to compare with the conventional model for estimating the MBF estimation, Monte Carlo techniques were used to simulate realistic dynamic PET studies based on kinetic parameters obtained from human studies with $^{18}$F-Flurpiridaz. The kinetic parameters were estimated as described above for kinetic analysis based on $^{18}$F-Flurpiridaz clinical data. Furthermore, the proposed models were evaluated for application to different vasodilator kinetics. The generation of simulated data was performed as follows: First, the NCAT torso phantom (Segars, W., et al., IEEE Trans. *Nucl. ScL* 46, 503-506, 2002) was used to generate static activity maps of the LV, RV, lung, liver, and the soft tissue. The heart activity maps were also generated with NCAT, with transmural defects in the LCX, RCA, and LAD territory and the rest of the myocardium is treated as the normal tissue. With those activity maps, high counts were simulated for each region with SIMSET (Harrison, R., et al., J. Nucl. Med. 34, 60, 1993), using a validated procedure for simulating the Philips Gemini System (Guerin, B., et al., *IEEE Trans. Nucl. Sci.* 55, 942-952, 2008). The simulated list-mode data were Fourier-rebinned into two-dimensional sinograms as 256×256 matrices over 87 slices. The simulated noise-free sinogram of each tissue type were then combined into a dynamic study by first scaling each sinogram with the corresponding time-activity curve and then summing those to form a simulated, noise-free sinogram for a dynamic PET study. The simulated study duration is 20 min, with the framing scheme of 6×5-s, 3×30-s, 5×60-s, 3×120-s, 6×5-s, 1×30-s, 2×60-s, 2×120-s frames. Then, Poisson deviates were added to the noise-free sinogram to form sinogram data with noise levels similar to those observed in clinical studies.

Dynamic PET studies were simulated with two different $^{18}$F-Flurpiridaz injection doses and two different vasodilators: adenosine and dipyridamole. 2 mCi was used for the $^{18}$F-Flurpiridaz dose for the first injection at time zero. The second injected dose was either 2 mCi (single-dose) or 4 mCi (double-dose) at 13 min after the first injection. $K_1(t)$ and $k_2(t)$ are both modeled as piecewise linear functions as Eqs. (4,5,6), respectively. For dipyridamole, the following timing information was used to simulate the data: $T_S=6.5$, $T_P=13$, $T_E=23$, and $T_B=29$ (minutes). The choice of $T_P$ and $T_E$ was based on the dipyridamole kinetics reported previously. For adenosine, the following timing information was used to simulate the data: $T_S=11.5$, $T_P=13$, $T_E=17.5$, and $T_B=20$. $T_P$ and $T_B$ were chosen based on the kinetics previously reported under a 6-min adenosine infusion ($T_E=T_S+6$).

For each combination of vasodilator and stress tracer dose, twenty noise realizations were simulated for each of the three simulated subjects. When simulating data for each subject, the kinetic parameters used to simulate the time-activity curve of a specific myocardial region were taken from the corresponding region of this specific subject. For example, the time-activity curve simulated the normal myocardium for the second subject is calculated with the parameters $K_{1,r}=0.738$, $k_{2,r}=0.108$, $K_{1,s}=2.292$, and $k_{2,s}=0.118$. In addition, for each noise realization, both the sinogram of a stress-only study and a single-scan rest/stress study were simulated. The stress-only study was later used as the reference for comparison.

After the sinograms were simulated with the previous steps, images were reconstructed with FBP (Hamming, cutoff=0.7) for 50 slices that cover the whole heart. In the normal myocardium and the three territories, a~2 mL ROI was used to calculate the time-activity curves. For each type of tissue and each combination of subject/vasodilator/stress dose, there are two time-activity curves per noise realization: the stress-only curve and rest/stress curve.

Parameter estimation was performed following extraction of the time-activity curves from the reconstructed images. Time-activity curves were fitted to the kinetic models previously described. First, the stress-only time-activity curve was used to estimate $K_{1,s}$ and $k_{2,s}$. The reference peak MBF was set to be equal to $K_{1,s}$ estimated from the stress-only time-activity curves. For the time-activity curves of the rest/stress study, the reference peak MBF was fitted to the MGH1 model in two steps: First, the portion of the time-activity curve before the vasodilator infusion was fitted to MGH1 for estimating $K_{1,r}$, $k_{2,r}$, $f_1$, and $f_{RV}$. After that, $K_{1,r}$, $k_{2,r}$, $f_1$, and $f_{RV}$ were fixed to values estimated from the previous step while $K_{1,s}$, $k_{2,s}$, $T_P$, $T_E$, and $T_B$ were estimated with Eqs. (4,5). The initial guess and bounds for parameter estimation are summarized in Table 2. Note that $T_B$ is not estimated for dipyridamole because $T_E$ is greater than 20 min, which is the total study duration.

TABLE 2

|  | $K_{1,r}$ | $k_{2,r}$ | $K_{1,s}$ | $k_{2,s}$ | $f_1$ | $f_{RV}$ | Dipyridamole | | Adenosine | | |
|---|---|---|---|---|---|---|---|---|---|---|---|
|  |  |  |  |  |  |  | $T_{P,S}$ | $T_{E,S}$ | $T_{P,S}$ | $T_{E,S}$ | $T_{B,S}$ |
| Initial guess | 0.5 | 0.1 | 1 | 0.1 | 0.05 | 0.05 | 11.5 | 23.5 | 12 | 17.6 | 19 |
| Lower bound | 0 | 0 | 0 | 0 | 0 | 0 | 8.5 | 21.5 | 11.5 | 17.5 | 18.5 |
| Upper bound | 5 | 0.3 | 10 | 0.3 | 0.25 | 0.25 | 14.5 | 26.5 | 13.5 | 18.5 | 21 |

For the MGH2 model, the same procedure was used for fitting the time-activity curves. The parameters $K_{1,r}$, $k_{2,r}$, $f_1$, and $f_{RV}$ were first estimated from the time-activity curve before vasodilator infusion and then fixed when estimating $K_{1,s}$, $k_{2,s}$. All the parameter estimation procedures were performed with COMKAT using the nonlinear weighted least squares with weights equal to the frame durations.

With respect to statistical analysis, for each combination of region/subject/vasodilator/stress dose, the sample mean and standard deviation of the estimated $K_{1,s}$ were computed over the twenty noise realizations. The $K_{1,s}$ estimated from the stress-only study was used as the reference. The mean and SD of $K_{1,s}$ from different models were plotted as bar graphs to compare the estimated results between those from the Standard method and those estimated from MGH1 and MGH2. For each vasodilator/stress dose combination, the average bias percentage was calculated by averaging the bias percentage either over the subjects or over the tissue types (four tissue types, three subjects). To evaluate the precision of MBF estimation for each model, the SD percentage was computed as follows: the SD was first calculated from the twenty noise realizations for each tissue type/subject/dose, and then divided by the mean of estimated MBF to form the relative SD percentage. Following that, the average SD percentage for each method was calculated by averaging over regions of the subjects. The average bias and SD percentages were plotted as bar graphs.

In conclusion, the present system and methods have shown with simulation studies that MBF can be accurately and precisely estimated from a single-scan rest/stress study for a long half-lived tracer such as $^{18}$F-Flurpiridaz. The rest/stress model requires a single input function for rest and stress, eliminating the need for extrapolation or subtraction. Accounting for the time-dependence of the kinetic parameters, the proposed models (MGH1 and MGH2) both achieve good accuracy and precision for different vasodilators and a range of different MBF states.

EXAMPLE 2

Advanced Modeling Approach

Aspects of the present system and methods relate to validation of sequential and concurrent rest-stress cardiac PET in acute ischemic porcine model. One approach involves validation of the measurement of myocardial blood flow in a sequential rest-stress study. The accuracy and precision with which MBF (in mL/g/min) can be measured is, in one example, evaluated in pigs using sequential rest-stress $^{18}$F-Flurpiridaz cardiac PET. Estimates of MBF obtained with the present approaches in dynamic $^{18}$F-Flurpiridaz are compared to flows measured with microspheres over a large range of flow values.

With respect to an example surgical protocol, eight domestic swine of either sex can be used. Endotracheal intubation and mechanical ventilation can be performed under general anesthesia. All pigs can be pre-medicated with the intravenous administration of thiamylal (22 mg/kg) prior to intubation and surgery. Anesthesia will be maintained with Halothane (0.5-1.5%), and a mixture of nitrous oxide (60%) and oxygen (40%). Central hemodynamics (e.g., arterial pH, $pCO_2$, $pO_2$) and ECG can be surveyed and maintained within the physiological range. A thoracotomy can be performed in the left fifth intercostal space to insert a catheter into the left atrium for injection of the microspheres. To induce the acute stenosis, the right internal carotid artery (RICA) in the neck can be isolated and surgical ties positioned 1 cm apart to permit control of bleeding when the vessel is incised. The RICA is used to insert a 7FR Amplatz catheter to engage the left anterior descending (LAD) coronary artery. A 3FR angioplasty balloon can be passed through the Amplatz catheter. The balloon can be guided under fluoroscopic control to the distal third of the LAD. The balloon catheter can be connected to a pressure gauge to monitor LAD pressure pre- and post-balloon inflation. During the inflation, a substantial pressure gradient can be create between the aorta and the coronary artery distal (−40 to 60 mmHg).

In one example, the balloon will occlude the LAD for 40 minutes or until the end of corresponding PET study.

A sequential rest-stress protocol, in one aspect, can involve two PET studies on separate days performed in each pig. On Day 1, the animal undergoes a dynamic PET study of $^{18}$F-Flurpiridaz for 60 minutes under the resting state without stenosis. Radioactive microspheres are injected via a catheter into left atrium, to provide a reference flow measurement. On Day 2, the pig is induced with a stenosis as described in the previous section. Once hemodynamic variables have stabilized, the animal is infused with dipyridamole intravenously for six minutes. Two different doses of dipyridamole (0.1 mg/kg/min and 0.2 mg/kg/min) are used to create different peak MBF with four pigs in each group. Blood pressure and heart rate are used to determine whether the peak hyperemia has been reached. Once the peak hyperemia has been reached, a dynamic PET study of $^{18}$F-Flurpiridaz is performed for 30 minutes accompanied by the injection of microspheres with a different radioisotope than those used in Day 1. During the PET study, 10 arterial blood samples are taken for measurement of the reference input function. At the end of the PET study the pigs are sacrificed and the excised hearts trimmed of the atria and right ventricle. The remaining left ventricle are cut into eight slices of equal thickness, and each of the myocardial slices are cut into eight radial sections, resulting in 64 myocardial segments of the heart. Tissue samples are counted in a well counter for measurement of microsphere flow after correction for background, decay and spillover.

Eight pigs can be used to measure sequential rest and stress myocardial blood flow. 4 pigs receive the 0.1 mg/kg and 4 receive the 0.2 mg/kg dipyridamole stress, resulting in 512 values of MBF in 8 pigs at baseline, 256 MBF values in 4 ischemic pigs at stress induced by 0.1 mg/kg of dipyridamole and 256 MBF values in 4 ischemic pigs at stress induced by 0.2 mg/kg. It can be determined if dynamic $^{18}$F-Flurpiridaz PET MBF measures in the 3 coronary territories can be strongly and positively (r>0.8) correlated with measures obtained using microspheres by correlation analysis.

In one example, the endpoints for analysis are PET measurements of local MBF obtained from the first 6, 10 and 60 minutes of PET scan. The 6 and 10 minute endpoints can use a simplified kinetic For each of the 64 myocardial segments, the MBF is measured from the microsphere activity as reference and read-out from the PET flow images by ROI analysis. The PET flow values for each method are entered into an ANOVA table classified by individual pig, segment, and measurement number.

The classification variables for the ANOVA can be segment and method; microspheres flow can be entered as a linear regressor. In some aspects, the data can be pooled into a single regression, independent of segment label. The mean values of MBF and standard error of the mean can be calculated for all myocardial blood flows estimated using the microspheres methodology as well as by dynamic $^{18}$F-Flurpiridaz. Results are displayed using the traditional polar map.

A further aspect of the present system and methods includes validation of the measurement of myocardial blood flow in a concurrent rest-stress study. After the validation of the measured MBF in sequential rest-stress $^{18}$F-Flurpiridaz cardiac PET studies, the measured MBF in a concurrent rest-stress study can be validated in pig models. The MBF measured by microsphere can be used as reference.

In another example of a surgical protocol, eight domestic swine of either sex are used. The same surgical procedure as described above can be used to incubate and anesthetize the animal. Acute myocardial ischemia can be induced. A catheter can be inserted into the left atrium for microsphere injection.

In another example of an experimental protocol, two injections of the $^{18}$F-Flurpiridaz are performed within the same imaging session for each pig. After the stenosis is induced and the hemodynamics of the animal become stable, the first $^{18}$F-Flurpiridaz dose (2 mCi) is injected when the animal is under the resting state. Microspheres are injected through the left atrial catheter at the time of peak stress. Six minutes after the first tracer injection, the pig is stressed with intravenous infusion of dipyridamole for a period of five minutes. Four pigs can undergo a 0.1 mg/kg/min infusion and the other four can undergo a 0.2 mg/kg/min infusion.

Hemodynamics, blood pressure and heart rate are continuously recorded and used to determine whether the peak hyperemia has been reached. Five minutes after the dipyridamole infusion, the second $^{18}$F-Flurpiridaz dose (2 mCi) is injected. Emission data is acquired for duration of 30 minutes including both the rest and stress studies accompanied by arterial blood sampling for measuring the reference input function. At the end of the PET study the pigs are sacrificed and myocardial samples are prepared and processed.

For each of the 64 myocardial segments, the MBF can be measured from the microsphere activity as reference and estimated from the PET images. The MBF can be estimated from concurrent rest-stress $^{18}$F-Flurpiridaz studies. Flow data is analyzed with a linear statistical model in which microsphere flow is entered as a linear regressor and segment is a classification variable. In one aspect, PET flow at rest and stress is linearly related to microsphere flow. The mean values of MBF and standard error of the mean are calculated for all MBFs estimated using the microspheres methodology as well as by dynamic $^{18}$F-Flurpiridaz. Results are displayed using polar maps.

In aspect of the present system and methods includes realistic Monte Carlo simulation of PET imaging. A realistic simulation of random coincidences, pixelated block detectors, light sharing among crystal elements and dead-time in 2D and 3D positron emission tomography (PET) imaging based on the SimSET Monte Carlo simulation software package has been developed and validated (Lewellen, T. K., et al., Monte Carlo simulations in nuclear medicine, 1998, 10P Publishing: Philadelphia. p. 77-92). The present simulation was validated by comparison to a Monte Carlo transport code widely used for PET modeling, GATE, and to measurements made on two GE Discovery STE PET scanners (Guerin, B. et al., *IEEE Nucl. Sci.*, 2008. 55(3): p. 942-952).

Figures 10A, 10B:
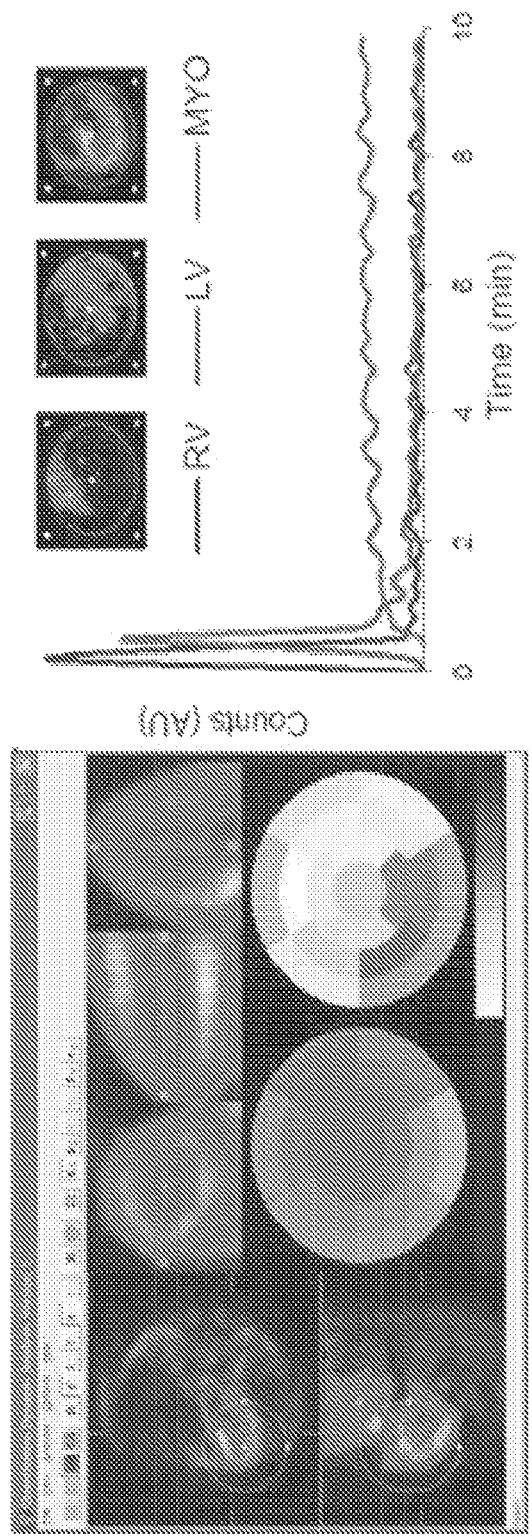
FIG. 10A is a screen capture of a user-friendly software developed for automated estimation of input functions using GFADS (Generalized Factor Analysis of Dynamic Sequences), as well as kinetic modeling of $^{82}$Rb, $^{13}$N-ammonia, $^{15}$O water and $^{18}$F-Flurpiridaz.
FIG. 10B is a graph that shows factors and factor images estimated with GFADS (note the good separation of LV, RV and myocardium). Data presented here were acquired with $^{18}$F-Flurpiridaz in a volunteer.

Another aspect of the present system and methods includes Quantitation of myocardial blood flow using generalized factor and compartment analyses (GFADS). Generalized factor analysis of dynamic sequences (GFADS) methods and software were developed specifically for the case of absolute quantitation of $^{18}$F-Flurpiridaz MBF as shown in FIGS. 10A-10B. The factor and compartment analyses are incorporated in a user friendly software that allows automated estimation of regional MBF. The intra- and inter-observer variability of MBF estimation was determined using $^{82}$Rb PET as well as the reproducibility of our GFADS +compartment analyses methodology (El Fakhri, G., et al., *J Nucl Med*, 2009. 50: p. 1062-1071; El Fakhri, G., et al., *J Nucl Med*, 2005. 46: p. 1264-1271; Anagnostopoulos, C., et al., *Eur J Nucl Med Mol Imag*, 2008. 35: p. 1593-1601; Curillova, Z., et al., *Eur J Nucl Med Mol Imag*, 2009. 35).

Figure 11A:
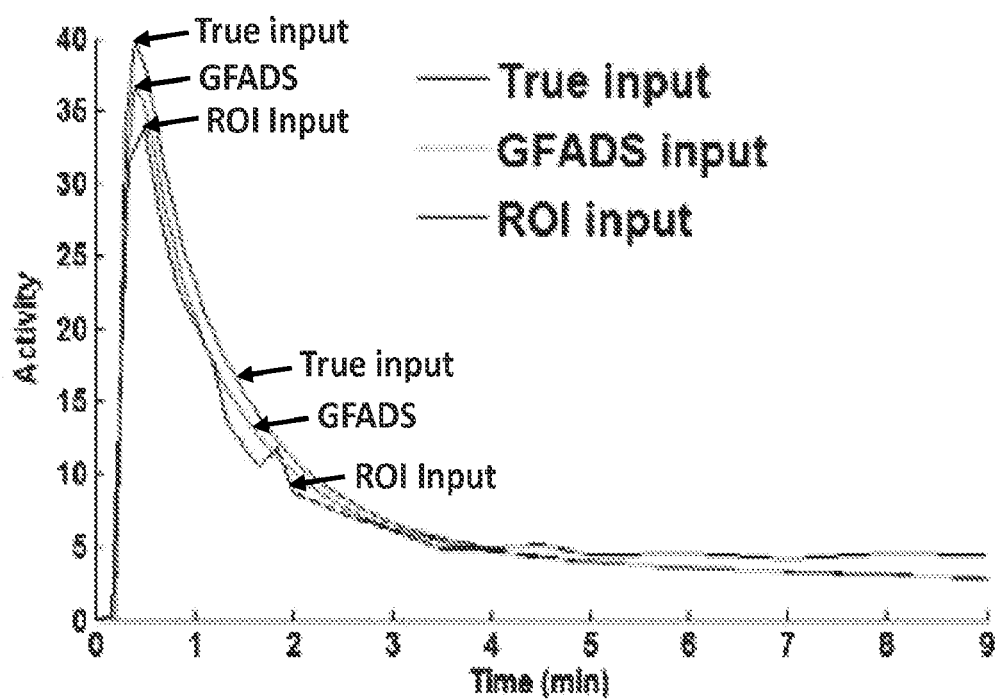
FIGS. 11A-11B are graphs that show a comparison of the RV and LV input functions derived with GFADS and ROIs (Regions of Interest) from simulation studies (FIG. 11A) and a monkey study (FIG. 11B). Compared to either the true input function in simulation or the blood samples in animal data, the GFADS input function has less partial volume effect and less contamination from spillover.
Figure 11B:
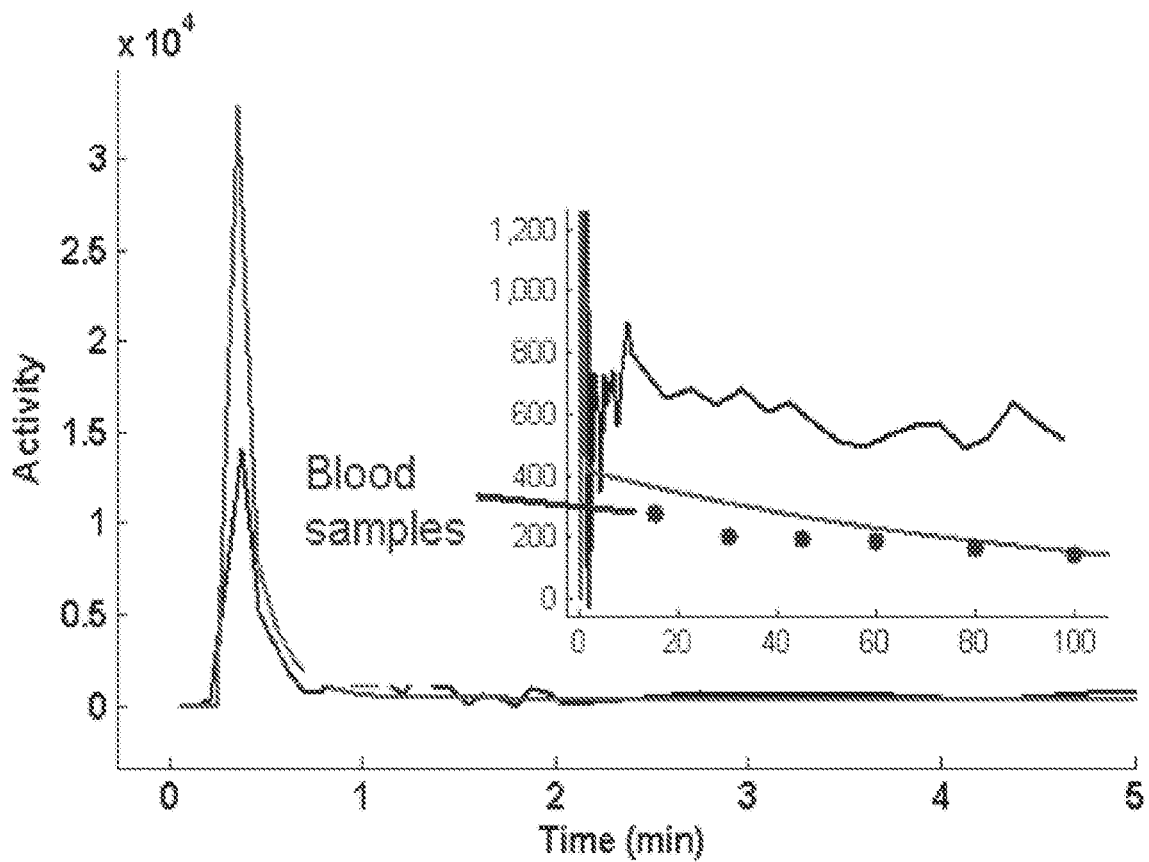

Yet another aspect of the present system and methods includes evaluating the effect of input functions estimation with GFADS and ROIs on MBF computation accuracy. The impact was assessed of the estimation of the $^{18}$F-Flurpiridaz input function, using GFADS versus manual region of interest (ROI), on the accuracy of myocardial blood flow quantitation (MBF) in realistic cardiac dynamic Monte Carlo simulations as well as cynomolgus monkey studies FIGS. 11A-11B show the reference left ventricular input function that was modeled in realistic dynamic Monte Carlo simulations as well as the estimated one with GFADS and using ROI. Compared to the "true" input functions used for simulation, the initial peaks of GFADS input functions are closer to the true input than the ROI-based input functions (due to less partial volume effect) and the tail of GFADS input aligns with the true input function very well (due to less spillover). The bias in MBF estimation, associated with the estimated LV and RV input functions, was 3.4±5.1% with GFADS and 18.2±7.7% with ROI. Similar conclusions are drawn from the monkey experiment where the GFADS LV factor was in much greater agreement with blood samples than the ROI TAC. The results showed that the MBF estimated with GFADS is more accurate than those obtained with ROI-based inputs.

Figure 12A:
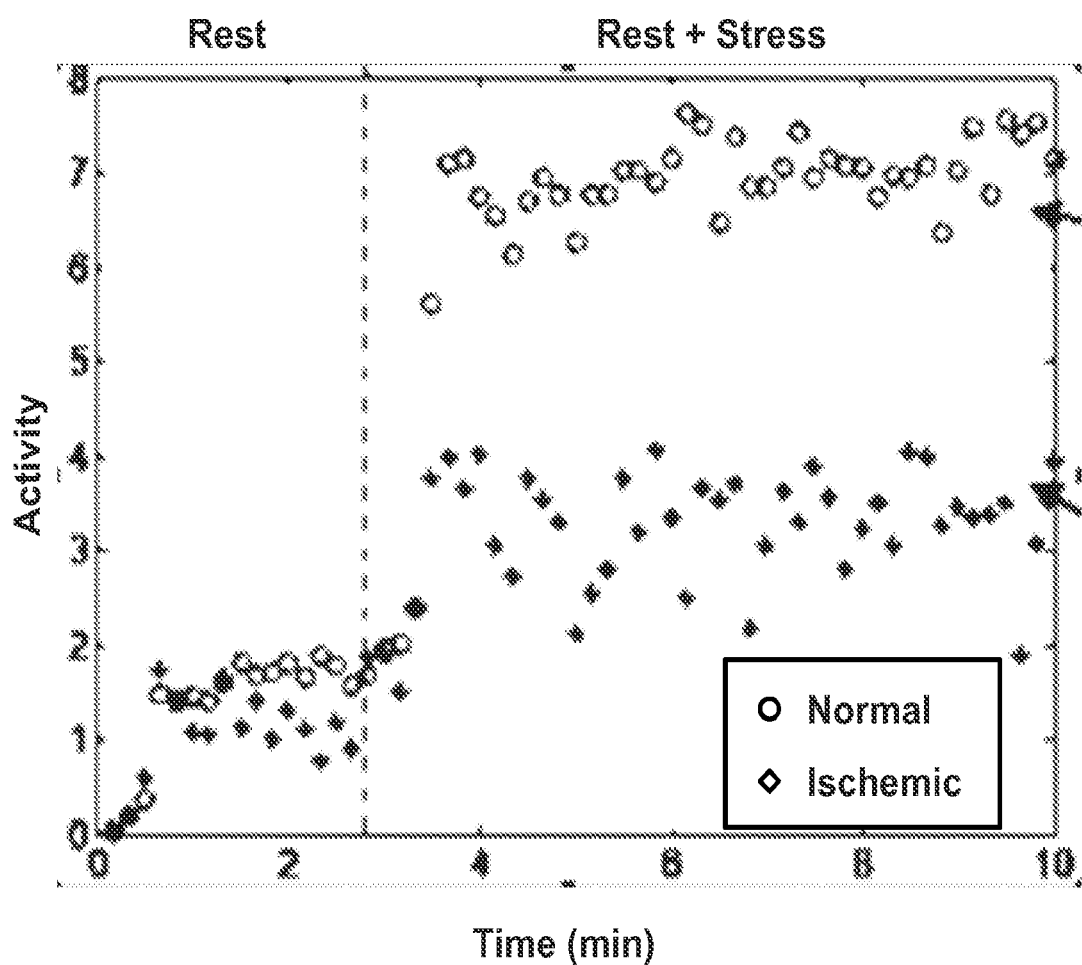
FIG. 12A is a scatter plot and FIG. 12B show data from a clinical cardiac study with $^{18}$F-Flurpiridaz. The TAC (Time-Activity Curve) in FIG. 12A shows the kinetics of the tracer uptake in healthy and ischemic myocardium under a concurrent rest-stress study.
Figure 12B:
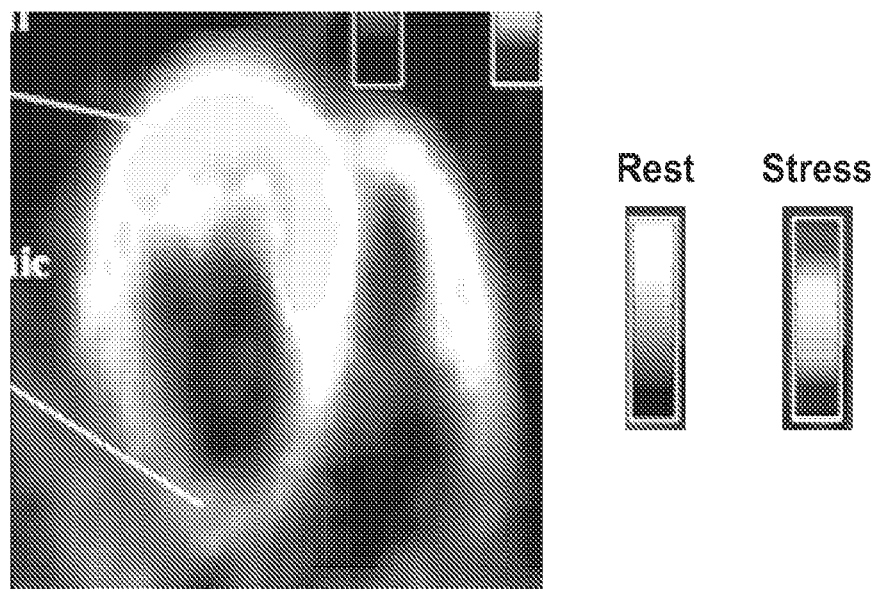

With respect to $^{18}$F-flurpiridaz patient studies, MBF was estimated with kinetic modeling analysis in a group of subjects in phase II clinical trial of $^{18}$F-Flurpiridaz. Rest and stress PET studies were performed sequentially on 10 healthy subjects and 6 CAD patients as shown in FIGS. 12A-12B. The estimated MBF data for rest-stress and healthy/ischemic myocardium are summarized in Table 3. Specifically, table 3 shows MBF (mL/g/min) estimated in clinical $^{18}$F-Flurpiridaz studies. Unlike ischemic MBF, normal MBF increased significantly during stress.

During the rest study, there was no significant difference in MBF (t-test, α=0.05) between the healthy and ischemic myocardium. However, during pharmacological stress, MBF increased more than 3× in healthy myocardium but remained approximately the same in ischemic regions. The MBF in ischemic myocardium showed no significant difference between rest and stress phases. The MBF measured with kinetic modeling for $^{18}$F-Flurpiridaz are consistent with the previously reported MBF measured with other tracers. The preliminary kinetic analysis of the $^{18}$F-Flurpiridaz shows that it has a high potential for absolute quantitation of MBF in clinical cardiac PET studies.

TABLE 3

|  | Healthy Subjects | Normal Myocardium in Patients | Ischemic Myocardium |
| --- | --- | --- | --- |
| Rest | 0.67 ± 0.01 | 0.73 ± 0.04 | 0.86 ± 0.06 |
| Stress | 2.84 ± 0.06 | 1.78 ± 0.07 | 0.73 ± 0.07 |

Figure 13:
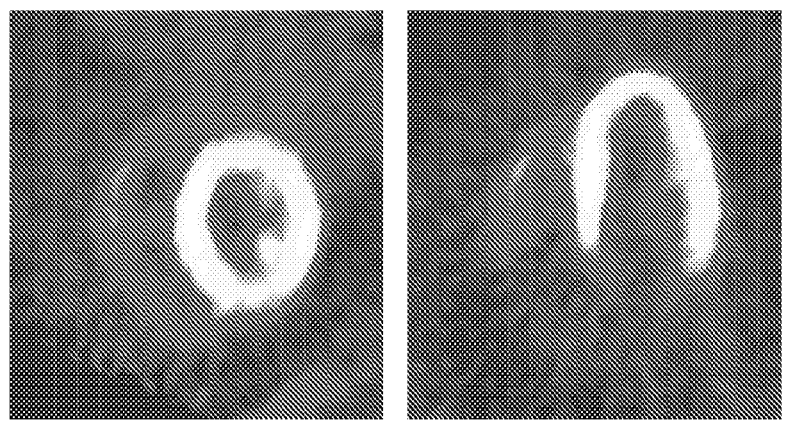
FIG. 13 is a set of images that show a short-axis and long-axis view of summed images from the monkey myocardium.

Still another aspect of the present system and methods includes $^{18}$F-Flurpiridaz myocardial blood flow estimation using dynamic PET in non-human primates. To evaluate the parameter precision when estimating the MBF, a long dynamic study was conducted on a 4.1-kg cynomolgus monkey and the MBF precision was examined with different durations of data being used for kinetic modeling. A dynamic $^{18}$F-Flurpiridaz imaging study was performed on a microPET P4. The animal was imaged under the resting state for 100 minutes with an injected dose of 1.25 mCi. FIG. 13 shows the summed images of the myocardium in the short and long axis. The LV (FIGS. 11A-11B) and RV input function were extracted with GFADS. Time-activity curve from a region of interest drawn over the myocardium was fitted to the 2-compartment model. The estimated parameters are: $K_1$=0.51 (SD=1.5%), $k_2$=0.075 (SD =4.7%), $k_3$ = 0.026 (SD=10.2%) and $k_4$ =0.016 (SD=10.4%). FIG. 14A shows the fitted time-activity curve. To evaluate the precision of $K_1$ and $k_2$, different study durations were used, ranging from one minute to 10 minutes to estimate $K_1$ and $k_2$ (with $k_3$ and $k_4$ fixed) as plotted for $K_1$ in FIG. 14B. With 10 minutes of data, both $K_1$ and $k_2$ were found to achieve a high precision (SD<10%), indicating that a concurrent rest/stress study of 30 minutes is sufficient to provide a reliable estimate of the MBF and the CFR. Furthermore, truncating the study duration to 3-10 min resulted in low bias in $K_1$ estimates (less than 4%) compared to using whole 100 minutes as shown in FIG. 14B. In addition, since the concentration curve is insensitive to $k_3$ and $k_4$ in the early frames of study, using nominal $k_3$ values between 0 and 0.1, was demonstrated to not bias the $K_1$ estimates more than 5% as in FIG. 14C.

Figure 15A:
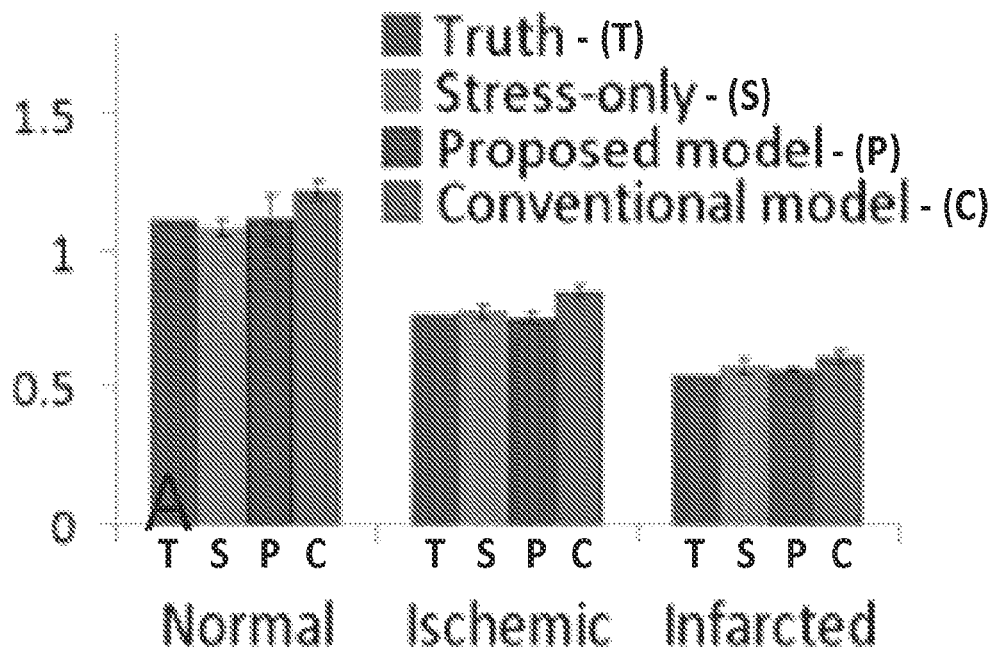
FIGS. 15A-15B are bar graphs that show a comparison of the estimated peak MBF with different models compared to the truth and the MBF from sequential rest-stress studies by simulation with (FIG. 15A) double 18F dose for stress and (FIG. 15B) single 18F dose for stress. The conventional model is based on the reported method (Rust, T. C., et al., *Phys. Med. Biol.*, 2006. 51: p. 5347-5362.).

A further aspect of the present system and methods includes concurrent rest-stress dynamic cardiac PET with Monte Carlo simulations. The accuracy and precision of the MBF estimated from the proposed concurrent rest-stress study was assessed with Monte Carlo simulations. The sinograms of different organs and myocardial defects were simulated with methods described herein. A dynamic PET study was simulated by the input functions and kinetic parameters from patient studies. During the rest study, MBF was simulated as 0.54 (mL/g/min) for all myocardial tissues. During stress, the simulated MBF are 1.1 (mL/g/min) for normal myocardium, 0.76 (mL/g/min) for ischemic myocardium and 0.54 (mL/g/min) for infarcted myocardium. The two different degrees of ischemic severity in all three coronary territories (LCX, LAD and RCA) was also simulated. The study duration and injection times were simulated according to the proposed scheme. Two injection doses were simulated: double dose for stress (2mCi for rest and 4 mCi for stress) and single stress dose (2 mCi for rest and 2mCi for stress.) The results of estimated MBF were plotted in FIGS. 15A-15B. With the present model, MBF was estimated reliably with a bias of less than 5% and the SD of less than 10% in both stress doses and in all the coronary territories.

Figure 15B:
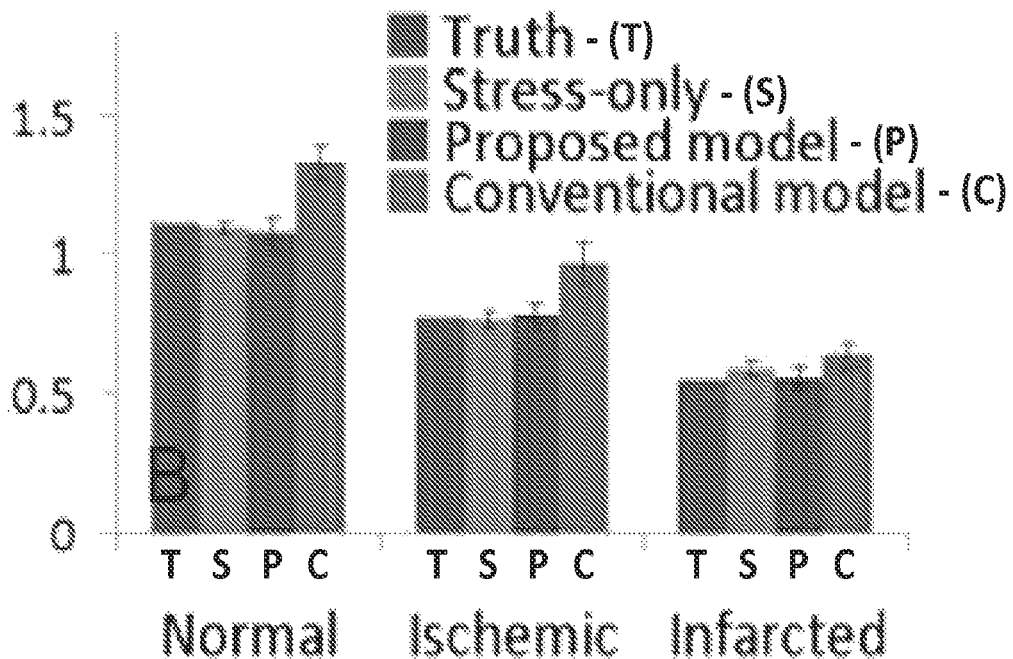

No significant difference was found in the MBF estimated with our model as compared to the MBF estimated from sequential rest-stress studies. As the conventional model does not accurately account for the effect of vasodilator in the model, it will overestimate the MBF during stress with 10-15% bias in the double-dose stress study as shown in FIG. 15A, and 20-30% bias in the single-dose stress study as shown in FIG. 15B. The data show that the present system and methods yield accurate kinetic parameter estimates for concurrent rest-stress that are not statistically different (NS) from sequential rest-stress.

Figure 16:
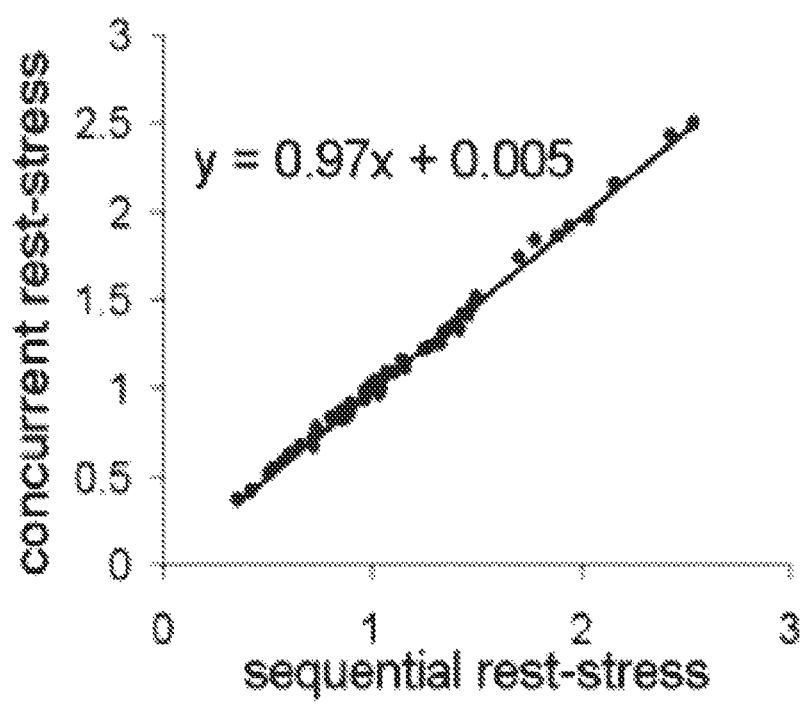
FIG. 16 is a graph that shows a correlation plot in synthetic clinical data between estimated MBF in concurrent and sequential rest-stress showing high correlation (r>0.9) and low bias (<3%).

Concurrent rest-stress cardiac PET with patient data simulations were also performed. The accuracy and precision of the MBF estimated from the proposed concurrent rest-stress study was assessed with simulations using clinical data. With the sequential rest-stress patient data, in which the rest and stress studies were performed in separate sessions, TACs were simulated under a concurrent rest-stress scenario. First, the kinetic parameters of $k_1$~$k_4$ were estimated from separate rest and stress studies. Following that, the original rest-only TAC was extended to include the effect of pharmacological stress using the proposed model and then added with Gaussian noise. This simulated TAC was summed with the stress-only TAC to form a TAC that mimics a TAC from a patient concurrent rest-stress study. FIG. 16 shows the plot of the regression analysis between the MBF estimated from sequential and concurrent rest-stress studies. A high correlation of R=0.99 and a slope of 0.98 was calculated. Clinical data show that the present system and methods allow accurate estimation of MBF in concurrent rest-stress.

Thus, in the foregoing, new systems and methods have been described. In one aspect, the approach is two-fold. In a first aspect, advances were made over prior methods by including more rigorous non-steady-state measurements. Specifically, two new dual-injection kinetic models have been developed that represent the response to pharmacological stress as a transitional or transient increase of MBF. The theory of the method is described and the feasibility of clinical measurement is evaluated by realistic simulation with an $^{18}$F flow tracer. In one aspect, $^{18}$F-Flurpiridaz, a new myocardial imaging agent now in Phase III trials is considered as the $^{18}$F flow tracer.

In a second aspect, the present system and methods address the need for adequate SNR in parametric images and a compelling application, one that can achieve wide clinical utilization. Automated indirect as well as direct parametric reconstruction can provide dramatic improvement of the SNR of parametric images, between 2× and 6× conventional methods. This is a general technique that has important applications in many organ systems beyond the heart.

With regard to the compelling application, there are several myocardial imaging agents that are in clinical trial. One example of an imaging agent is $^{18}$F-Flurpiridaz, which is now under Phase III study. $^{18}$F-Flurpiridaz has nearly complete first-pass extraction in the coronary circulation, which can be an important factor in selecting a myocardial flow tracer. For the first few minutes after injection, the distribution of $^{18}$F-Flurpiridaz depends almost entirely on coronary blood flow; later, the distribution depends on both flow and binding to mitochondrial complex I. Methods previously developed for flow measurement with $^{82}$Rb, and $^{13}$N are informative but not optimal given the kinetics and 110 minute half-life of $^{18}$F-Flurpiridaz studies.

Current analytic methods assume that a pharmacological stress challenge induces a new steady state with respect to blood flow, one that persists, unchanged, throughout the imaging session. But in reality pharmacological stress increases flow which rises to a plateau and then declines, as opposed to exhibiting steady-state behavior. Accordingly, the flow should be considered to be time dependent. In a first embodiment, the present system and method have shown that the assumption of time dependence significantly reduces bias in the measurement. In one aspect, a more realistic kinetic measurement strategy allows for rest and stress imaging to be conducted in a single imaging session lasting about 30 minutes. The analysis derives a single rest-stress input function (without operator intervention) using generalized factor analysis (GFADS). Rest and stress blood flow are estimated jointly from a single rest-stress data set. In one example, a single rest-stress $^{18}$F-based imaging session can be completed in about 30 minutes, yielding absolute rest and stress blood estimates with high accuracy and low noise.

In certain embodiments, the present system provides for completion of a rest-stress imaging session in a single visit requiring only 30 minutes imaging time. In other embodiments, all of the proposed techniques are incorporated into a software system that can run unattended, so that clinical or research staff may concentrate on throughput and patient interactions.

In still other embodiments, the present system provides a direct parametric reconstruction capable of quantitative parametric imaging from listmode data. A computationally feasible direct parametric reconstruction (DPR) approach acting on listmode projections and incorporating quantitative corrections for attenuation, detector sensitivity, scatter and random coincidences can yield parametric maps that are significantly less noisy than those obtained with the traditional indirect approach (image reconstruction +pixel-by-pixel time activity curve (TAC) fitting). This strategy is applicable to dynamic cardiac imaging with $^{18}$F-based tracers such as $^{18}$F-Flurpiridaz. However, similar gains in other organs, such as the brain are also possible. The drastic reduction in noise with this technique is due to the use of temporal regularization in the DPR process and the more correct modeling of the noise statistics in the projection than in the image domain. High-quality parametric maps of the myocardium can be obtained while significantly lowering the injected dose (and therefore rest-stress spillover and radiation dose to the patient). It has been demonstrated that DPR allows for injection of a low activity dose in the rest part of the concurrent rest-stress protocol, making it easier to estimate rest and stress myocardial parametric maps in a single imaging session. In another aspect, the noise reduction benefit of DPR is extendable to concurrent rest-stress flow mapping. One advance is the implementation of DPR to directly estimate kinetic parameters from listmode data while correcting for the effects of scatter, randoms, detector sensitivity, and the like.

The present methods can be evaluated in an acute ischemic porcine model. The experiments are sequential. This approach allows for the demonstration of the in vivo validity of the methodological developments and provides the information needed to undertake human studies.

The present invention has been described in terms of one or more preferred embodiments, and it should be appreciated that many equivalents, alternatives, variations, and modifications, aside from those expressly stated, are possible and within the scope of the invention.

Each reference identified in the present application is herein incorporated by reference in its entirety.

While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

What is claimed is:

1. A system for performing a single-scan rest-stress cardiac measurement, the system comprising:
    a positron emission tomography (PET) imaging system configured to acquire PET imaging data from a subject having received a first PET radiotracer associated with a rest state and a second PET radiotracer associated with a stress state;
    a processor having non-transitory computer readable media programmed with instructions to cause the processor to:
    generate PET images of the subject administered with the first and second PET radiotracer from the PET imaging data,
    process the PET images with a non-steady-state, multi-compartment parametric model, the parametric model representing a response to pharmacological stress as a time-varying increase of myocardial blood flow and the parametric model comprising a plurality of time-varying transport rates configured to account for effects of the pharmacological stress during the stress state on both the first PET radiotracer associated with the rest state and the second PET radiotracer associated with the stress state, wherein the parametric model further comprises a single input function for both the first and the second PET radiotracers, and
    generate a report indicating an output of the non-steady-state, multi-compartment parametric model indicating a measure of the myocardial blood flow for both the rest state and the stress state of the subject.

2. The system of claim 1, wherein the PET imaging system is configured to acquire the PET imaging data during a single scan session of less than an hour in duration.

3. The system of claim 1, wherein at least one of the first and the second PET radiotracers has a half-life of at least 60 minutes.

4. The system of claim 3, wherein at least one of the first and the second PET radiotracers is an 18F-based tracer.

5. The system of claim 4, wherein the $^{18}$F-based tracer is $^{18}$F-Flurpiridaz.

6. A system for estimating kinetic parameters of myocardial blood flow of a subject, the system comprising:
    a processor having non-transitory computer readable media programmed with instructions to cause the processor to:
    obtain PET image data from the subject, the PET image data acquired and timed with at least one real-time measurement of a physiological variance of the subject;
    estimate the kinetic parameters within a kinetic region of interest in the PET image data based on a model accessed from the non-transitory computer readable media, the kinetic parameters based on an expression of a radiotracer within the PET image data, the model representing a response to stress as a time-varying increase of myocardial blood flow, wherein the radiotracer within the PET image data includes radiotracer administered during a rest state and radiotracer administered during a stress state and the model comprises a plurality of time-varying transport rates configured to account for effects of the stress during the stress state on both the radiotracer administered during the rest state and the radiotracer administered during the stress state, wherein the model further comprises a single input function for both the radiotracer administered during the rest state and the radiotracer administered during the stress state; and
    generate a report of at least one kinetic parameter of the kinetic parameters of myocardial blood flow based on the kinetic parameters estimated from the PET image data.

7. The system of claim 6, wherein the kinetic parameters are further based on a real-time measurement of physiological variance of the subject.

8. The system of claim 7, wherein the at least one real-time measurement of a physiological variance of the subject comprises a computation of ventricle input functions.

9. The system of claim 8, wherein the computation of ventricle input functions comprises generalized factor analysis and dynamic orthogonal grouping.

10. The system of claim 6, wherein the model is capable of executing a direct parametric reconstruction (DPR) of the kinetic region of interest.

11. The system of claim 10, wherein the DPR comprises incorporation of time-of-flight information pertaining to the PET images.

12. The system of claim 6, wherein the at least one kinetic parameter of blood flow comprises myocardial blood flow during both the rest state and the stress states of the subject.

13. The system of claim 12, wherein the radiotracer administered during the stress state is administered following administration of a pharmacological stressor to the subject during peak hyperemia.

14. The system of claim 12, wherein the stress state is induced pharmacologically.

15. The system of claim 6, wherein the PET image data is acquired within a total time period of about 30 minutes or less.

16. The system of claim 6, wherein the radiotracer permits multi-compartment kinetic modeling and has an extraction fraction of at least 90%, resulting in long tissue residence periods.

17. The system of claim 16, wherein the radiotracer comprises 18F-Flurpiridaz.

* * * * *

UNITED STATES PATENT AND TRADEMARK OFFICE
CERTIFICATE OF CORRECTION

PATENT NO. : 11,730,430 B2
APPLICATION NO. : 14/429178
DATED : August 22, 2023
INVENTOR(S) : Nathaniel Alpert et al.

It is certified that error appears in the above-identified patent and that said Letters Patent is hereby corrected as shown below:

In the Specification

Column 13, Line 45, "lida et al." should be --Iida et al.--.

Column 13, Line 45, "(lida," should be --(Iida,--.

Column 21, Line 62, "for and equal to $x \geq 0$ for $x^2$" should be --for $x \geq 0$ and equal to $x^2$--.

Column 33, Line 29, "10P" should be --IOP--.

Signed and Sealed this
Seventh Day of November, 2023

*Katherine Kelly Vidal*

Katherine Kelly Vidal
*Director of the United States Patent and Trademark Office*